(12) United States Patent
Miwa

(10) Patent No.: US 6,196,974 B1
(45) Date of Patent: Mar. 6, 2001

(54) BLOOD-PRESSURE MONITORING APPARATUS

(75) Inventor: Yoshihisa Miwa, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/396,462

(22) Filed: Sep. 15, 1999

(30) Foreign Application Priority Data

Oct. 7, 1998 (JP) .................................................. 10-285357

(51) Int. Cl.$^7$ ...................................................... A61B 5/00
(52) U.S. Cl. ........................... 600/490; 600/485; 600/494; 600/500
(58) Field of Search ........................... 600/481, 483–485, 600/490, 492–495, 500–502, 526

(56) References Cited

U.S. PATENT DOCUMENTS

| 5,131,391 | 7/1992 | Sakai et al. . |
| 5,671,750 | * 9/1997 | Shinoda ............................ 600/485 X |
| 5,738,612 | * 4/1998 | Tsuda ................................ 600/485 X |
| 5,752,920 | 5/1998 | Ogura et al. . |
| 5,776,071 | * 7/1998 | Inukai et al. ...................... 600/485 X |
| 5,876,348 | * 3/1999 | Sugo et al. ........................ 600/485 X |
| 5,906,581 | * 5/1999 | Tsuda ................................ 600/490 X |
| 6,007,492 | * 12/1999 | Goto et al. ............................ 600/485 |

* cited by examiner

Primary Examiner—Cary O'Connor
Assistant Examiner—Ryan Carter
(74) Attorney, Agent, or Firm—Oliff & Berridge, PLC

(57) ABSTRACT

A blood-pressure monitoring apparatus including a measuring device which includes an inflatable cuff adapted to apply a pressing pressure to a first body portion of a living subject and which measures a blood-pressure value of the living subject by changing the pressing pressure of the inflatable cuff, a blood-pressure-relating-information obtaining device which iteratively obtains a piece of blood-pressure-relating information which changes in relation to a change of the blood pressure of the living subject, a starting device for starting, when the obtained blood-pressure-relating information satisfies a predetermined condition with respect to at least one reference value, a blood-pressure measurement of the measuring device, and a display device which displays a first graphical representation of the obtained blood-pressure-relating information, and a second graphical representation of the reference value, so that the first graphical representation can be compared with the second graphical representation by the living subject such as a patient or a different person such as a doctor or nurse.

18 Claims, 10 Drawing Sheets

BLOOD-PRESSURE MONITORING APPARATUS

BACKGROUND OF THE INVENTION

1. Field of the Invention

The present invention relates to a blood-pressure monitoring apparatus which monitors a blood pressure of a living subject based on information which changes in relation to the change of blood pressure of the subject.

2. Related Art Statement

As information relating to a pulse wave which propagates through an arterial vessel of a living subject, there are known a pulse-wave-propagation time DT and a pulse-wave-propagation velocity $V_M$ (m/s). The pulse-wave-propagation time DT is a time which is needed by the pulse wave to propagate between two different positions of the arterial vessel. Additionally, it is known that the above pulse-wave-propagation-relating information is, within a predetermined range, substantially proportional to the blood pressure ("BP", mmHg) of the living subject. Hence, there has been proposed a BP monitoring apparatus which determines, in advance, coefficients α, β in the following expression: EBP=α(DT)+β (where a is a negative constant and β is a positive constant), or EBP=α($V_M$)+β (where α and β are positive constants), based on two measured BP values of the subject and two measured pulse-wave-propagation time values (DT) or two measured pulse-wave-propagation velocity values ($V_M$), iteratively determines an estimated BP value EBP of the subject, based on each piece of subsequently obtained pulse-wave-propagation-relating information, according to the above-indicated first or second expression, and starts a BP measurement using an inflatable cuff when an estimated BP value EBP has changed by not less than a predetermined amount or proportion from a prior value EBP determined at the time of the last BP measuring operation.

A relationship between pulse-wave-propagation-relating information and estimated BP value BP, represented by the above-indicated first or second expression, changes depending upon the condition of a central organ of the living subject (e.g., the condition of cardiac muscle) and/or the condition of a peripheral organ of the subject (e.g., the hardness of peripheral blood vessels, or the resistance of those vessels to the blood flow). Thus, there has been proposed a BP monitoring apparatus which obtains hertbeat-relating information (e.g., heart rate or pulse period) as central-organ-relating information, and peripheral-pulse-wave-area-relating information as peripheral-organ-relating information and which starts a BP measurement using an inflatable cuff when the pulse-wave-propagation-relating information (or the estimated BP value EBP calculated based on the pulse-wave-propagation-relating information) has changed by not less than a predetermined amount or proportion from the time of the last BP measuring operation and simultaneously when at least one of the hertbeat-relating information and the peripheral-pulse-wave-area-relating information has changed by not less than a predetermined amount or proportion from the time of the last BP measuring operation. An example of this BP monitoring apparatus is disclosed in U.S. Pat. No. 5,752,920.

However, the prior BP monitoring apparatuses as described above display only a digital value indicative of each piece of BP-relating information which is used in judging whether or not to start a BP measurement using the cuff, or a trend graph representing a timewise change of a plurality of pieces of BP-relating information. From only those items, however, the subject or a medical person who attends to the subject cannot judge whether the BP of the subject is near to, or is changing toward, a state in which a BP measurement using the cuff is started. Accordingly, the medical person can not give any treatments to the subject before a BP measurement using the cuff is actually started.

SUMMARY OF THE INVENTION

It is therefore an object of the present invention to provide a blood-pressure monitoring apparatus which monitors the blood pressure of a living subject based on information which changes in relation to the change of blood pressure of the subject and which enables a user to judge whether the blood pressure of the subject is near to the state in which a blood-pressure measurement using an inflatable cuff is started.

The present invention provides a blood-pressure monitoring apparatus which has one or more of the technical features that are described below in respective paragraphs given parenthesized sequential numbers (1) to (18). Any technical feature which includes another technical feature shall do so by referring, at the beginning, to the parenthesized sequential number given to that technical feature.

(1) According to a first feature of the present invention, there is provided a blood-pressure monitoring apparatus comprising a measuring device which includes an inflatable cuff adapted to apply a pressing pressure to a first body portion of a living subject and which measures a blood-pressure value of the living subject by changing the pressing pressure of the inflatable cuff, a blood-pressure-relating-information obtaining device which iteratively obtains a piece of blood-pressure-relating information which changes in relation to a change of the blood pressure of the living subject, starting means for starting, when the obtained blood-pressure-relating information satisfies a predetermined condition with respect to at least one reference value, a blood-pressure measurement of the measuring device, and a display device which displays a first graphical representation of the obtained blood-pressure-relating information, and a second graphical representation of the reference value, so that the first graphical representation is comparable with the second graphical representation. A user such as the living subject or a person who attends to the subject can judge or recognize, from a positional relationship between the first graphical represetation of the obtained blood-pressure-relating information, and the second graphical representation of the reference value, on the display device, whether or not the blood pressure of the subject is near to the state in which the starting means starts a blood-pressure measurement of the measuring device using the inflatable cuff.

(2) According to a second feature of the present invention that includes the first feature (1), the blood-pressure-relating-information obtaining device comprises means for iteratively calculating a blood-pressure-relating value which changes in relation to a change of the blood pressure of the living subject, and the starting means comprises means for starting the blood-pressure measurement of the measuring device, when a value based on the calculated blood-pressure-relating value satisfies the predetermined condition with respect to two reference values that the value based on the calculated blood-pressure-relating value does not fall within an alarm range having an upper limit value defined by one of the two reference values and a lower limit value defined by the other of the two reference values. The alarm range may be replaced with a single alarm value according to the fourth or sixth feature (4) or (6) described below.

(3) According to a third feature of the present invention that includes the second feature (2), the display device comprises means for displaying, with the first and second graphical representations, a third graphical representation of an alert range which is contained in the alarm range and is narrower than the alarm range, so that the first graphical representation is comparable with the second and third graphical representations. The fact that the value based on the calculated blood-pressure-relating value falls within the alarm range but does not fall within the alert range, indicates that the blood pressure of the subject needs alerting of the subject or the person who attends to the subject. Thus, the user can more easily judge, from the first to third representations displayed on the display device, whether or not the blood pressure of the subject is near to the state in which the starting means starts a blood-pressure measurement of the measuring device. The alert range may be replaced with a single alert value according to the fifth or seventh feature (5) or (7) described below.

(4) According to a fourth feature of the present invention that includes the first feature (1), the blood-pressure-relating-information obtaining device comprises means for iteratively calculating a blood-pressure-relating value which changes in relation to a change of the blood pressure of the living subject, and the starting means comprises means for starting the blood-pressure measurement of the measuring device, when a value based on the calculated blood-pressure-relating value satisfies the predetermined condition with respect to the reference value that the value based on the calculated blood-pressure-relating value is greater than the reference value.

(5) According to a fifth feature of the present invention that includes the fourth feature (4), the display device comprises means for displaying, with the first and second graphical representations, a third graphical representation of an alert value which is smaller than the reference value, so that the first graphical representation is comparable with the second and third graphical representations.

(6) According to a sixth feature of the present invention that includes the first feature (1), the blood-pressure-relating-information obtaining device comprises means for iteratively calculating a blood-pressure-relating value which changes in relation to a change of the blood pressure of the living subject, and the starting means comprises means for starting the blood-pressure measurement of the measuring device, when a value based on the calculated blood-pressure-relating value satisfies the predetermined condition with respect to the reference value that the value based on the calculated blood-pressure-relating value is smaller than the reference value.

(7) According to a seventh feature of the present invention that includes the sixth feature (6), the display device comprises means for displaying, with the first and second graphical representations, a third graphical representation of an alert value which is greater than the reference value, so that the first graphical representation is comparable with the second and third graphical representations.

(8) According to an eighth feature of the present invention that includes any one of the first to seventh features (1) to (7), the blood-pressure-relating-information obtaining device comprises means for successively calculating, in synchronism with each of successive heartbeats of the living subject, a blood-pressure-relating value which changes in relation to a change of the blood pressure of the living subject, and the display device comprises change displaying means for displaying, with the first and second graphical representations, a third graphical representation of a value relating to a change of each of the successively calculated blood-pressure-relating values, from a value based on at least one prior value of the successively calculated blood-pressure-relating values. In this case, the use can more accurately judge, from the first to third representations displayed on the display device, whether or not the blood pressure of the subject is near to, or is changing toward, the state in which the starting means starts a blood-pressure measurement of the measuring device.

(9) According to a ninth feature of the present invention that includes the eighth feature (8), the change displaying means comprises means for displaying the third graphical representation comprising an arrow which is rotatable from a predetermined original angle by an angle indicative of the value relating to the change of the each of the successively calculated blood-pressure-relating values.

(10) According to a tenth feature of the present invention that includes the eighth feature (8), the change displaying means comprises means for displaying the third graphical representation of a ratio of an amount of change of the each blood-pressure-relating value from a prior blood-pressure-relating value which immediately precedes the each blood-pressure-relating value, to the prior blood-pressure-relating value.

(11) According to an eleventh feature of the present invention that includes any one of the first to tenth features (1) to (10), the blood-pressure-relating-information obtaining device comprises a pulse-wave-propagation-relating-information obtaining device which iteratively obtains a piece of pulse-wave-propagation-relating information relating to propagation of a pulse wave through an arterial vessel of the living subject, relationship determining means for determining a relationship between pulse-wave-propagation-relating information and blood pressure, based on at least one blood-pressure value of the living subject measured by the measuring device and at least one piece of pulse-wave-propagation-relating information obtained by the pulse-wave-propagation-relating-information obtaining device, and estimating means for estimating a blood-pressure value of the living subject, based on each piece of pulse-wave-propagation-relating information of a plurality of pieces of pulse-wave-propagation-relating information obtained by the pulse-wave-propagation-relating-information obtaining device, according to the determined relationship between pulse-wave-propagation-relating information and blood pressure.

(12) According to a twelfth feature of the present invention that includes the eleventh feature (11), the blood-pressure-relating-information obtaining device further comprises average calculating means for calculating, as the obtained blood-pressure-relating information, an average of a plurality of blood-pressure values estimated by the estimating means.

(13) According to a thirteenth feature of the present invention that includes the eleventh feature (11), the blood-pressure-relating-information obtaining device further comprises change-value calculating means for calculating, as the obtained blood-pressure-relating information, a value relating to a change of a first blood-pressure value estimated by the estimating means from a second blood-pressure value estimated prior to the first estimated blood-pressure value by the estimating means.

(14) According to a fourteenth feature of the present invention that includes any one of the first to thirteenth features (1) to (13), the blood-pressure-relating-information obtaining device comprises at least one of pulse-wave-propagation-time calculating means for iteratively calculating, as the obtained blood-pressure-relating information, a pulse-wave propagation time which is needed for each of a plurality of heartbeat-synchronous pulses of a pulse wave to propagate between two portions of an arterial vessel of the living subject, and pulse-wave-propagation-velocity calculating means for iteratively calculating, as the obtained blood-pressure-relating information, a pulse-wave propagation velocity at which each of a plurality of heartbeat-synchronous pulses of a pulse wave propagates between two portions of an arterial vessel of the living subject.

(15) According to a fifteenth feature of the present invention that includes any one of the first to fourteenth features (1) to (14), the blood-pressure-relating-information obtaining device comprises at least one of pulse-period calculating means for iteratively calculating, as the obtained blood-pressure-relating information, a pulse period equal to a time interval between each pair of successive heartbeat-synchronous pulses of a pulse wave obtained from the living subject, and pulse-wave-area-relating-value calculating means for iteratively calculating, as the obtained blood-pressure-relating information, a pulse-wave-area-relating value relating to an area of each of a plurality of heartbeat-synchronous pulses of a pulse wave obtained from the living subject.

(16) According to a sixteenth feature of the present invention that includes any one of the first to fifteenth features (1) to (15), the blood-pressure-relating-information obtaining device comprises at least one of an electrocardiographic-pulse-wave detecting device which includes a plurality of electrodes adapted to be put on a plurality of portions of the living body and detects an electrocardiographic pulse wave including a plurality of heartbeat-synchronous pulses, from the subject via the electrodes, and a photoelectric-pulse-wave detecting device which is adapted to be worn on a second body portion of the living subject, and which emits a light toward the second body portion and obtains a photoelectric pulse wave including a plurality of heartbeat-synchronous pulses, from the light received from the second body portion.

(17) According to a seventeenth feature of the present invention that includes any one of the first to sixteenth features (1) to (16), the display device comprises means for displaying the first graphical representation of the obtained blood-pressure-relating information, and the second graphical representation of the reference value, in a two-dimensional coordinate system which is defined by a first axis indicative of time and a second axis indicative of blood-pressure-relating information.

(18) According to an eighteenth feature of the present invention that includes any one of the first to seventeenth features (1) to (17), the blood-pressure-relating-information obtaining device comprises means for iteratively obtaining three sorts of blood-pressure-relating information each of which changes in relation to a change of the blood pressure of the living subject, and the display device comprises means for displaying the first graphical representation of each of the obtained three sorts of blood-pressure-relating information, and the second graphical representation of each of three reference values respectively corresponding to the three sorts of blood-pressure-relating information, in a three-dimensional coordinate system which is defined by a first axis indicative of a first one of the three sorts of blood-pressure-relating information, and a second axis indicative of a second one of the three sorts of blood-pressure-relating information, and a third axis indicative of a third one of the three sorts of blood-pressure-relating information.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
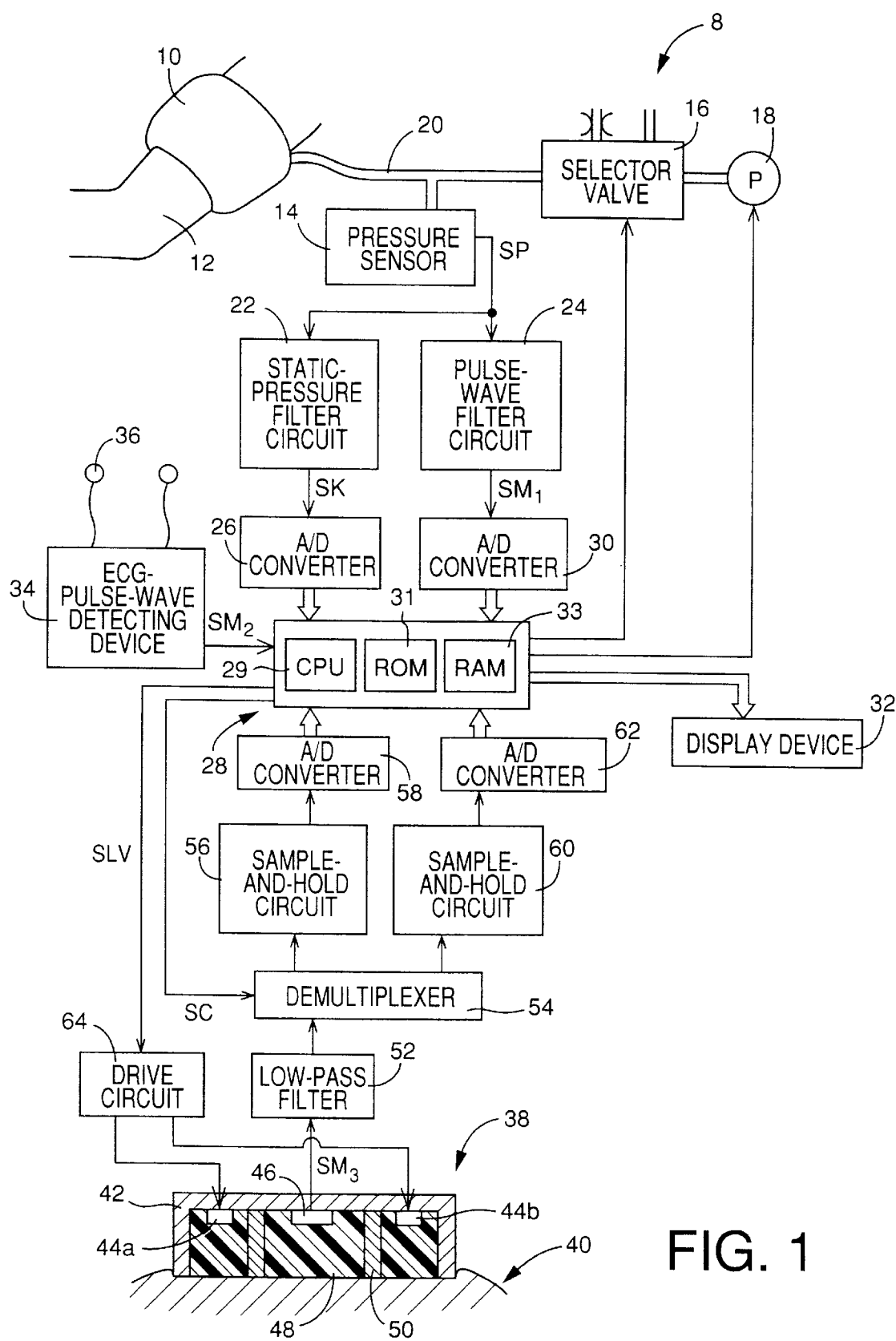
FIG. 1 is a diagrammatic view of a blood-pressure ("BP") monitoring apparatus embodying the present invention.

Referring to FIG. 1, there will be described a blood-pressure ("BP") monitoring apparatus 8 embodying the present invention.

In FIG. 1, the BP monitoring apparatus 8 includes an inflatable cuff 10 which has a belt-like cloth bag and a rubber bag accommodated in the cloth bag and which is adapted to be wrapped around, e.g., a right upper arm 12 of a patient as a living subject, and a pressure sensor 14, a selector valve 16 and an air pump 18 each of which is connected to the cuff 10 via piping 20. The selector valve 16 is selectively placed in an inflation position in which the selector valve 16 permits a pressurized air to be supplied from the air pump 18 to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the inflatable cuff 10, and supplies a pressure signal SP representative of the detected pressure to each of a static-pressure filter circuit 22 and a pulse-wave filter circuit 24. The static-pressure filter circuit 22 includes a low-pass filter and extracts, from the pressure signal SP, a static component contained in the signal SP, i.e., cuff-pressure signal SK representative of the static cuff pressure. The cuff-pressure signal SK is supplied to an electronic control device 28 via an analog-to-digital ("A/D") converter 26. The pulse-wave filter circuit 24 includes a band-pass filter and extracts, from the pressure signal SP, an oscillatory component having predetermined frequencies, i.e., cuff-pulse-wave signal $SM_1$. The cuff-pulse-wave signal $SM_1$ is supplied to the control device 28 via an A/D converter 30. The cuff-pulse-wave signal $SM_1$ is representative of the cuff pulse wave, i.e., oscillatory pressure wave which is produced from a brachial artery (not shown) of the patient in synchronism with the heartbeat of the patient and is propagated to the inflatable cuff 10.

The control device 28 is provided by a so-called microcomputer including a central processing unit ("CPU") 29, a read only memory ("ROM") 31, a random access memory ("RAM") 33, and an input-and-output ("I/O") port (not shown). The CPU 29 processes signals according to control programs pre-stored in the ROM 31 by utilizing a temporary-storage function of the RAM 33, and supplies drive signals to the selector valve 16 and the air pump 18 through the I/O port.

The BP monitoring apparatus 8 further includes an electrocardiographic (ECG) pulse wave detecting device 34 which continuously detects an ECG pulse wave representative of the action potential of cardiac muscle of the patient, through a plurality of electrodes 36 being put on predetermined body portions of the patient, and supplies an ECG-pulse-wave signal $SM_2$ representative of the detected ECG pulse wave, to the control device 28. The ECG-pulse-wave detecting device 34 is used for detecting a Q-wave or an R-wave of the waveform of each heartbeat-synchronous pulse of the ECG pulse wave that corresponds to a time point when the outputting of blood from the heart of the patient toward the aorta is started. Thus, the ECG-pulse-wave detecting device 34 functions as a first pulse-wave detecting device.

The BP monitoring apparatus 8 further includes a photoelectric-pulse-wave detecting probe 38 (hereinafter, referred to as the "probe" 38) which is employed as part of a pulse oximeter. The probe 38 functions as a second pulse-wave detecting device, or a peripheral-pulse-wave detecting device for detecting a peripheral pulse wave propagated to a peripheral artery including capillaries. The probe 38 is set on a skin or a body surface 40 of the patient, e.g., an end portion of a finger of a left hand of the patient with the help of a band (not shown), such that the probe 38 is held in close contact with the body surface 40. The probe 38 is worn on the hand of one arm different from the other arm around which the cuff 10 is wrapped.

The probe 38 includes a container-like housing 42 which opens in a certain direction, a first and a second group of light emitting elements 44a, 44b, such as LEDs (light emitting diodes), which are disposed on an outer peripheral portion of an inner bottom surface of the housing 42 (hereinafter, referred to as the light emitting elements 44 in the case where the first and second groups of light emitting elements 44a, 44b need not be discriminated from each other), a light receiving element 46, such as a photodiode or a phototransister, which is disposed on a central portion of the inner bottom surface of the housing 42, a transparent resin 48 which is integrally disposed in the housing 42 to cover the light emitting elements 44 and the light receiving element 46, and an annular shading member 50 which is disposed between the light emitting elements 44 and the light receiving element 46, for preventing the light receiving element 46 from receiving the lights emitted toward the body surface 40 by the light emitting elements 44 and directly reflected from the body surface 40.

The first group of light emitting elements 44a emit a first light having a first wavelength whose absorbance changes depending on a blood oxygen saturation value of the patient. The first elements 44a emit, e.g., a red light having about 660 nm wavelength. The second group of light emitting elements 44b emit a second light having a second wavelength whose absorbance does not change depending on the blood oxygen saturation value of the patient. The second elements 44b emit, e.g., an infrared light having about 800 nm wavelength. The first and second light emitting elements 44a, 44b alternately emit the red and infrared lights, respectively, at a predetermined frequency, e.g., a relatively high frequency of several hundred Hz to several thousand Hz. The lights emitted toward the body surface 40 by the light emitting elements 44 are reflected from a body tissue of the patient where a dense capillaries occur, and the reflected lights are received by the common light receiving element 46. In place of the 660 nm and 800 nm lights, the first and second light emitting elements 44a, 44b may employ various pairs of lights each pair of which have different wavelengths, so long as one light of each pair exhibits significantly different absorption factors with respect to oxygenated hemoglobin and reduced hemoglobin, respectively, and the other light exhibits substantially same absorption factors with respect to the two sorts of hemoglobin, i.e., has a wavelength which is reflected by each of the two sorts of hemoglobin.

The light receiving element 46 outputs, through a low-pass filter 52, a photoelectric-pulse-wave signal $SM_3$ representative of an amount of the first or second light received from the body tissue of the patient. The light receiving element 46 is connected to the low-pass filter 52 via an amplifier or the like. The low-pass filter 52 removes, from the photoelectric-pulse-wave signal $SM_3$ input thereto, noise having frequencies higher than that of a pulse wave, and outputs the noise-free signal $SM_3$, to a demultiplexer 54. The photoelectric-pulse-wave signal $SM_3$ is representative of a photoelectric pulse wave which is produced in synchronism with the pulse of the patient.

The demultiplexer 54 is switched according to signals supplied thereto from the control device 28 in synchronism with the alternate light emissions of the first and second light emitting elements 44a, 44b. Thus, the demultiplexer 54 separates the photoelectric-pulse-wave ("PPW") signal $SM_3$ into two PPW signals which correspond to the first and second lights, respectively. More specifically described, the demultiplexer 54 successively supplies, to the I/O port (not shown) of the control device 28, a first PPW signal $SM_R$ representative of the red light having the first wavelength through a first sample-and-hold circuit 56 and an A/D converter 58, and a second PPW signal $SM_{IR}$ representative of the infrared light having the second wavelength through a second sample-and-hold circuit 60 and an A/D converter 62. The first and second sample-and-hold circuits 56, 60 hold the first and second PPW signals $SM_R$, $SM_{IR}$ input thereto, respectively, and do not output the current signals $SM_R$, $SM_{IR}$ to the A/D converters 58, 62, before the prior signals $SM_R$, $SM_{IR}$ are completely converted by the A/D converters 58, 62, respectively.

In the control device 28, the CPU 29 carries out a measuring operation according to control programs pre-stored in the ROM 31 by utilizing the temporary-storage function of the RAM 33. More specifically described, the CPU 29 generates a light emit signal SLV to a drive circuit 64 so that the first and second light emitting elements 44a, 44b alternately emit the red and infrared lights at a predetermined frequency, respectively, such that each light emission lasts for a predetermined duration. In synchronism with the alternate light emissions of the first and second light emitting elements 44a, 44b, the CPU 29 generates a switch signal SC to the demultiplexer 54 to switch the demultiplexer 54 between its first and second positions. Thus, the PPW signal $SM_3$ is separated by the demultiplexer 54 such that the first PPW signal $SM_R$ is supplied to the first sample-and-hold circuit 56 while the second PPW signal $SM_{IR}$ is supplied to the second sample-and-hold circuit 60. The CPU 29 determines the degree of saturation of oxygen in the blood of the body tissue of the patient, based on the two PPW signals $SM_R$, $SM_{IR}$, according to a predetermined expression pre-stored in the ROM 31. An example of blood oxygen saturation determining method is disclosed in U.S. Pat. No. 5,131,391.

Figure 2:
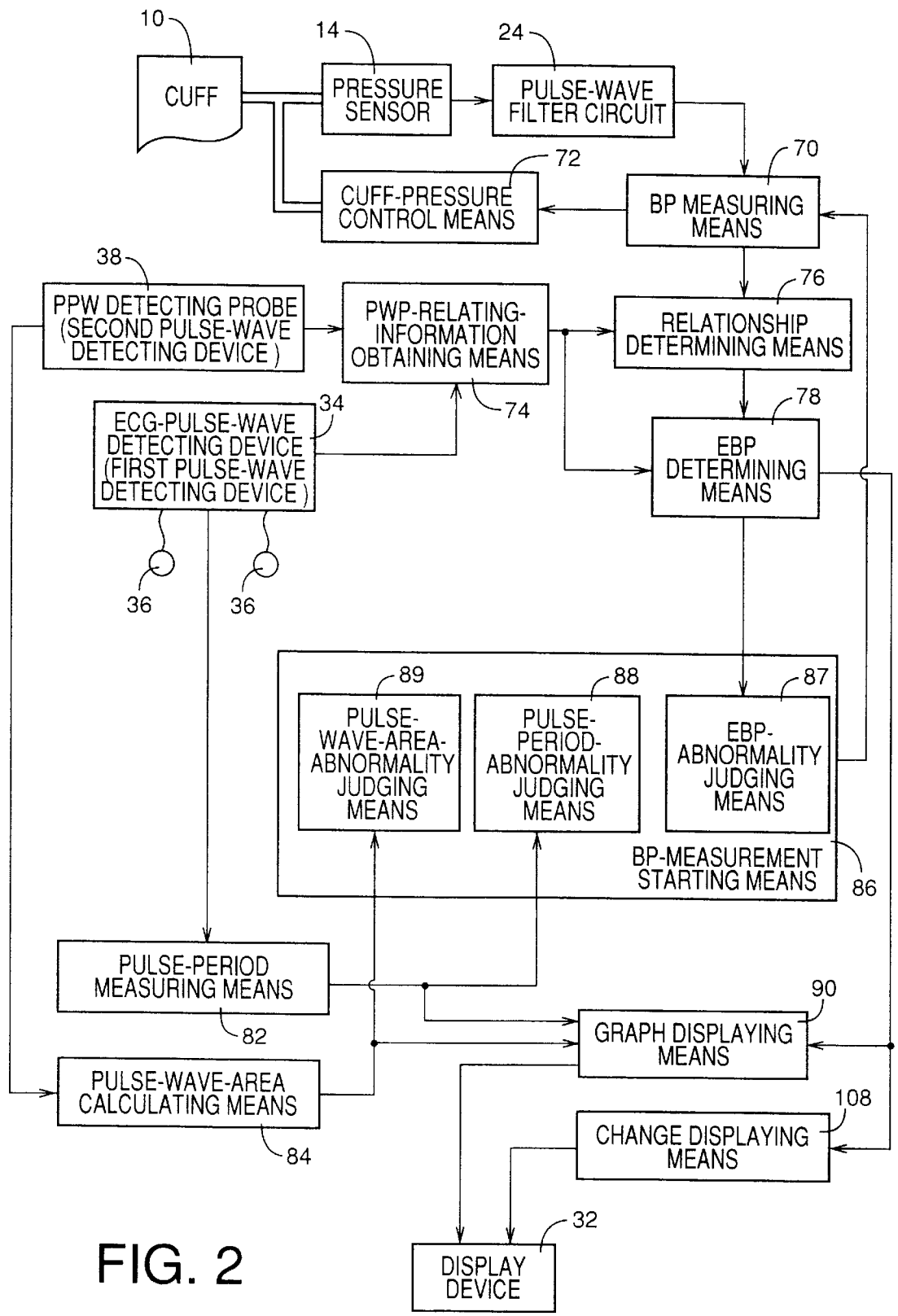
FIG. 2 is a block diagram for illustrating essential functions of an electronic control device of the apparatus of FIG. 1.

FIG. 2 illustrates essential functions of the control device 28 of the present BP monitoring apparatus 8. In the figure, a BP measuring means or circuit 70 measures a systolic, a mean, and a diastolic BP value $BP_{SYS}$, $BP_{MEAN}$, $BP_{DIA}$ of the patient, according to a well known oscillometric method, based on variation of respective amplitudes of heartbeat-synchronous pulses of the pulse wave represented by the cuff-pulse-wave signal $SM_1$ obtained while the cuff pressure which is quickly increased by a cuff-pressure control means or circuit 72 to a target pressure value $P_{CM}$ (e.g., 180 mmHg), is slowly decreased at a predetermined rate, e.g., the rate of about 3 mmHg/sec.

Figure 3:
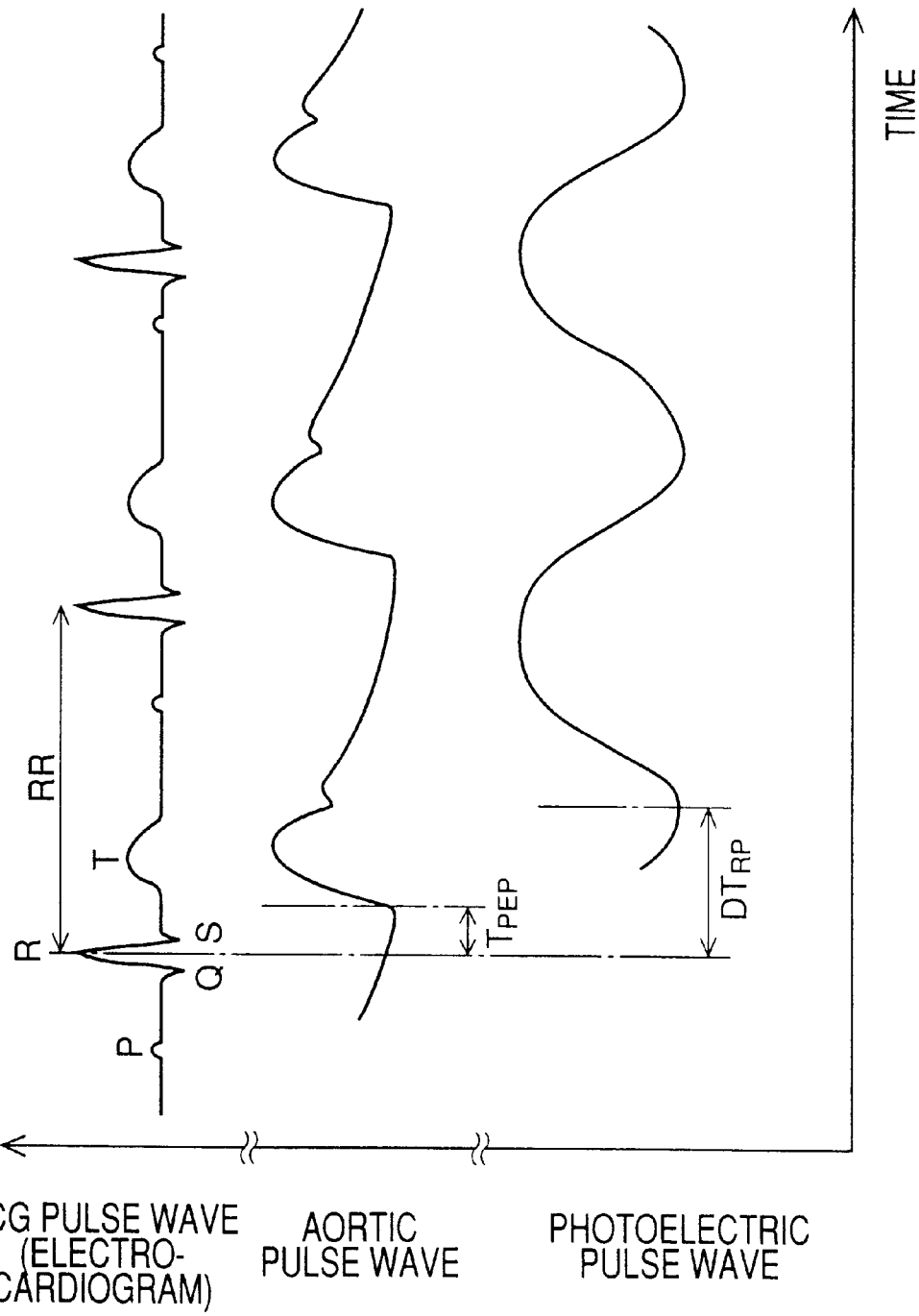
FIG. 3 is a view for illustrating a pulse-wave-propagation time value $DT_{RP}$ obtained by an operation of the control device of the apparatus of FIG. 1.

A pulse wave propagation ("PWP") relating information obtaining means or circuit 74 as part of BP-relating-information obtaining means or circuit includes a time-difference calculating means or circuit which iteratively calculates, as a PWP time $DT_{RP}$, a time difference between a predetermined point (e.g., R-wave) on the waveform of each of periodic pulses of the ECG pulse wave that are detected by the ECG-pulse-wave detecting device 34 and a predetermined point (e.g., rising point, i.e., minimum point) on the waveform of a corresponding one of periodic pulses of the photoelectric pulse wave ("PPW") that are detected by the probe 38, as illustrated in FIG. 3. The PPW-relating-information obtaining means 74 iteratively calculates a PWP velocity $V_M$ (m/sec) of a pulse wave propagated through an artery of the patient, based on the calculated PPW time $DT_{RP}$, according to the following expression (1) pre-stored in the ROM 31:

$$V_M = L/(DT_{RP} - T_{PEP}) \qquad (1)$$

where L (m) is a length of the artery as measured from the left ventricle to the position where the probe 38 is set, via the aorta; and $T_{PEP}$ (sec) is a pre-ejection period between the R-wave of the waveform of each pulse of the ECG pulse wave and the minimum point of the waveform of a corresponding pulse of an aortic pulse wave.

The values L, $T_{PEP}$ are constants, and are experimentally obtained in advance.

A relationship determining means or circuit 76 determines two coefficients α, β in the following second or third expression (2) or (3), based on two systolic BP values $BP_{SYS}$ measured by the BP measuring means 70, and two PWP time values $DT_{RP}$ or two PWP velocity values $V_M$ calculated by the PPW-relating-information obtaining means 74. Each value $DT_{RP}$, $V_M$ may be an average of several values $DT_{RP}$, $V_M$ which are obtained immediately before each BP measurement. The above two expressions (2), (3) generally define a relationship between PWP time value $DT_{RP}$ and estimated BP value EBP, and a relationship between PWP velocity value $V_M$ and estimated BP value EBP, respectively. In place of the above-indicated relationship between estimated systolic BP value $BP_{SYS}$ and either one of PWP time value $DT_{RP}$ and PWP velocity value $V_M$, a relationship between estimated mean or diastolic BP value $EBP_{MEAN}$, $EBP_{DIA}$ and either one of PWP time value $DT_{RP}$ and PWP velocity value $V_M$ may be employed. In short, a relationship between PWP-relating information and estimated BP value EBP may be determined depending upon which one of systolic, mean, and diastolic BP value is selected as estimated BP value EBP, i.e., monitored BP value.

$$EBP = \alpha(DT_{RP}) + \beta \qquad (2)$$

where α is a negative constant and β is a positive constant.

$$EBP = \alpha(V_M) + \beta \qquad (3)$$

where α and β are positive constants.

An estimated-BP ("EBP") determining means or circuit 78 as part of the BP-relating-information obtaining means iteratively determines an estimated BP value EBP of the patient, based on either one of an actual PWP time value $DT_{RP}$ and an actual PWP velocity value $V_M$ iteratively obtained by the PWP-relating-information obtaining means 74, according to the relationship represented by the second or third expression (2) or (3).

Figure 5:
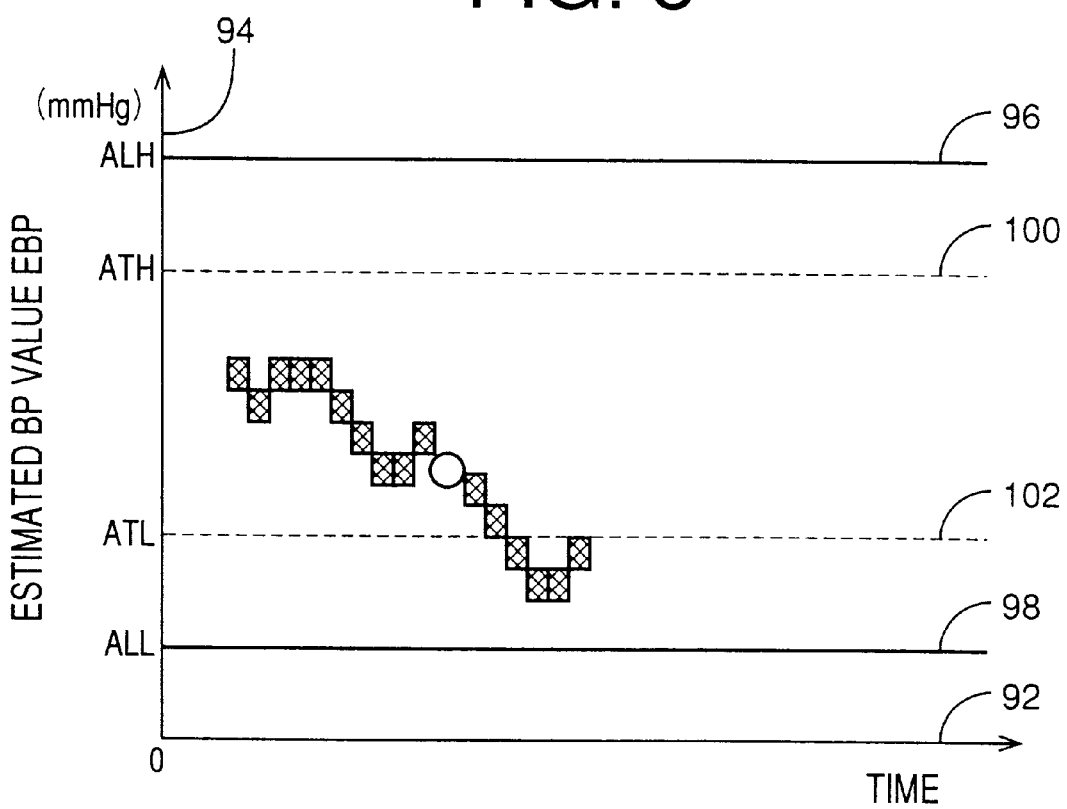
FIG. 5 is a view for illustrating a trend graph of moving averages of estimated BP values that is displayed by a display device of the apparatus of FIG. 1.

The control device 28 controls a display device 32 to display a trend graph of moving averages (described later) of the estimated BP values EBP along a horizontal axis indicative of time, as shown in FIG. 5, so that the trend graph can be observed by a medical person, such as a doctor or a nurse, who attends to the patient.

A pulse-period measuring means or circuit 82 as part of the BP-relating-information obtaining means iteratively measures a pulse period value RR by measuring or calculating a time difference between respective predetermined points (e.g., R-waves) of each pair of successive heartbeat-synchronous pulses of the ECG pulse wave detected by the ECG-pulse-wave detecting device 34.

Figure 4:
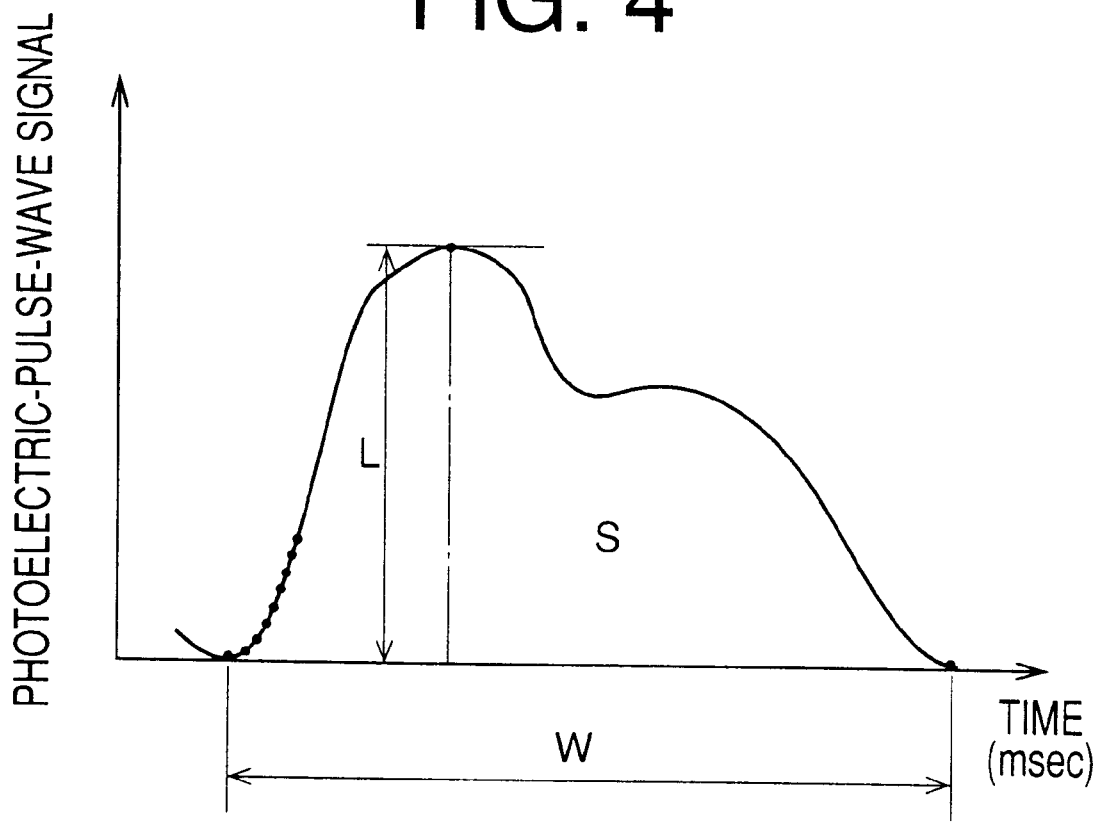
FIG. 4 is a view for explaining the manner in which a normalized pulse-wave area value VR is obtained.

A pulse-wave-area calculating means or circuit 84 as part of the BP-relating-information obtaining means iteratively calculates a pulse-wave area value VR by normalizing an area S defined or enveloped by the waveform of each heartbeat-synchronous pulse of the PPW detected by the probe 38, based on a period W and an amplitude L of the each pulse. More specifically described, as shown in FIG. 4, the waveform of each pulse of the PPW is defined by a series of data points indicative of respective magnitudes which are input at a predetermined short interval such as several milliseconds to several tens of milliseconds. The pulse-wave area S is obtained by integrating, over the period W of the each pulse, respective magnitudes of the data points of the each pulse, and then a normalized pulse-wave area value VR is obtained according to the following expression: VR=S/(W X L). The normalized pulse-wave area value VR is a dimensionless value indicative of the ratio of the pulse-wave area S to a rectangular area defined by the period W and the amplitude L of the each pulse. For this parameter, the symbol "% MAP" may be used in place of the symbol "VR".

A BP-measurement starting means or circuit 86 starts a BP measurement of the BP measuring means 70, when the absolute value of at least one value based on at least one estimated BP value EBP is not smaller than a first reference (i.e., alarm) value $AL_{EBP}$. For example, the BP-measurement starting means 86 may start a BP measurement of the BP measuring means 70, when the respective absolute values of not less than twenty successive values based on not less than twenty successive estimated BP values EBP are not smaller than the first alarm value $AL_{EBP}$, and simultaneously when the respective absolute values of not less than twenty successive values based on not less than twenty successive measured pulse period values RR are not smaller than a second reference (alarm) value $AL_{RR}$ or when the respective absolute values of not less than twenty successive values based on not less than twenty successive calculated pulse-wave area values VR are not smaller than a third reference (alarm) value $AL_{VR}$. A value based on each estimated BP value EBP may be the each value EBP itself, a moving average of a plurality of values EBP including the each value EBP, or a change value that is an amount of change of the each value EBP from a "control" value EBP determined at the time of the last BP measuring operation, or the ratio of the amount of change to the "control" value EBP. Similarly, a value based on each measured pulse period value RR may be the each value RR itself, a moving average of a plurality of values RR including the each value RR, or a change value that is an amount of change of the each value RR from a "control" value RR measured at the time of the last BP measuring operation, a moving average of a plurality of values VR including the each value VR, or the ratio of the amount of change to the "control" value RR, and a value based on each calculated pulse-wave area value VR may be the each value VR itself, or a change value that is an amount of change of the each value VR from a "control" value VR calculated at the time of the last BP measuring operation, or the ratio of the amount of change to the "control" value VR.

More specifically described, the BP-measurement starting means 86 includes an EBP-abnormality judging means or circuit 87 for judging that each estimated BP value EBP determined by the EBP determining means 78 is abnormal when at least one value based on at least one value EBP including the each value EBP does not fall within a first reference (alarm) range $ALH_{EBP}$–$ALL_{EBP}$; an RR-abnormality judging means or circuit 88 for judging that each pulse period value RR measured by the pulse-period measuring device 82 is abnormal when at least one value based on at least one value RR including the each value RR does not fall within a second reference (alarm) range $ALH_{RR}$–$ALL_{RR}$; and a VR-abnormality judging means or circuit 89 for judging that each pulse-wave area value VR calculated by the pulse-wave area calculating means 84 is abnormal when at least one value based on at least one value VR including the each value VR does not fall within a third reference (alarm) range $ALH_{RR}$–$ALL_{RR}$. When the EBP-abnormality judging means 87 judges that an estimated BP value EBP is abnormal and simultaneously at least one of the RR-abnormality judging means 88 and the VR-abnormality judging means 89 judges that a corresponding one of a pulse period value RR and a pulse-wave area value VR is abnormal, the BP-measurement starting means 86 starts a BP measurement of the BP measuring means 70. However, the single first alarm range $ALH_{EBP}$–$ALL_{EBP}$ may be replaced with two first alarm ranges, i.e., a wide first alarm range and a narrow first alarm range which is completely contained in the wide first alarm range and is narrower than the same. Similarly, the single second alarm range $ALH_{RR}$–$ALL_{RR}$ may be replaced with two second alarm ranges, i.e., a wide second alarm range and a narrow second alarm range which is completely contained in the wide second alarm range and is narrower than the same, and the single third alarm range $ALH_{VR}$–$ALL_{VR}$ may be replaced with two third alarm ranges, i.e., a wide third alarm range and a narrow third alarm range which is completely contained in the wide third alarm range and is narrower than the same. In the latter case, the user can select a desired one of the two first, second, or third alarm ranges, through operation of keys (not shown) provided on the monitoring apparatus 8.

Meanwhile, each of the first, second, and third alarm ranges $ALH_{EBP}$–$ALL_{EBP}$, $ALH_{RR}$–$ALL_{RR}$, $ALH_{VR}$–$ALL_{VR}$ may be replaced with only one of the upper and lower limit values $ALH_{EBP}$, $ALL_{EBP}$, $ALH_{RR}$, $ALL_{RR}$, $ALH_{VR}$, $ALL_{VR}$ of the each range. For example, the first to third alarm ranges may be replaced with only the respective upper limit values $ALH_{EBP}$, $ALH_{RR}$, $ALH_{VR}$ thereof, or with only the respective lower limit values $ALL_{EBP}$, $ALL_{RR}$, $ALL_{VR}$ thereof. However, the single first upper limit value $ALH_{EBP}$ may be replaced with two first upper limit values, i.e., a great or high first upper limit value and a small or low first upper limit value, and the single first lower limit value $ALL_{EBP}$ may be replaced with two first lower limit values, i.e., a great or high first lower limit value and a small or low first lower limit value. Similarly, the single second upper limit value $ALH_{RR}$ may be replaced with two second upper limit values, i.e., a great or high second upper limit value and a small or low second upper limit value, the single second lower limit value $ALL_{RR}$ may be replaced with two second lower limit values, i.e., a great or high second lower limit value and a small or low second lower limit value, the single third upper limit value $ALH_{VR}$ may be replaced with two third upper limit values, i.e., a great or high third upper limit value and a small or low third upper limit value, and the single third lower limit value $ALL_{VR}$ may be replaced with two third lower limit values, i.e., a great or high third lower limit value and a small or low third lower limit value. In the latter case, the user can select a desired one of the two first, second, or third upper limit values, and a desired one of the two first, second, or third lower limit values, through operation of keys (not shown) provided on the monitoring apparatus 8.

A graph displaying means or circuit 90 displays, on the display device 32 (e.g., cathode ray tube), a graph including at least one of respective graphical representations of a value based on an estimated BP value determined by the EBP determining means 78, a value based on a pulse period value RR measured by the pulse-period measuring means 82, and a value based on a pulse-wave area value VR calculated by the pulse-wave-area calculating means 84, and at least one of respective graphical representations of the first alarm range $ALH_{EBP}$–$ALL_{EBP}$, the second alarm range $ALH_{RR}$–$ALL_{RR}$, and the third alarm range $ALH_{VR}$–$ALL_{VR}$, so that a user such as the patient or the medical person can compare at least one of the respective values based on the three values EBP, RR, VR to a corresponding one of the three alarm ranges. Each of the respective values based on the three values EBP, RR, VR is a piece of BP-relating information which changes in relation to a change of the BP of the patient and which is utilized by the BP-measurement starting means 86 in judging whether or not to start a BP measurement of the BP measuring means 70.

The graph displaying means 90 additionally displays, in the same graph, at least one of respective graphical representations of a first alert range $ATH_{EBP}$–$ATL_{EBP}$, a second alert range $ATH_{RR}$–$ATL_{RR}$, and a third alert range $ATH_{VR}$–$ATL_{VR}$, so that the user can compare at least one of the respective values based on the three values EBP, RR, VR to a corresponding one of the three alert ranges. Each of the three alert ranges $ATH_{EBP}$–$ATL_{EBP}$, $ATH_{RR}$–$ATL_{RR}$, $ATH_{VR}$–$ATL_{VR}$ is completely contained in, and is narrower than, a corresponding one of the three alarm ranges $ALH_{EBP}$–$ALL_{EBP}$, $ALH_{RR}$–$ALL_{RR}$, $ALH_{VR}$–$ALL_{VR}$. Like the three alarm ranges $ALH_{EBP}$–$ALL_{EBP}$, $ALH_{RR}$–$ALL_{RR}$, $ALH_{VR}$–$ALL_{VR}$, the single first alert range $ATH_{EBP}$–$ATL_{EBP}$ may be replaced with two first alert ranges, i.e., a wide first alert range and a narrow first alert range which is completely contained in the wide first alert range and is narrower than the same, the single second alert range $ATH_{RR}$–$ATL_{RR}$ may be replaced with two second alert ranges, i.e., a wide second alert range and a narrow second alert range which is completely contained in the wide second alert range and is narrower than the same, and the single third alert range $ATH_{VR}$–$ATL_{VR}$ may be replaced with two third alert ranges, i.e., a wide third alert range and a narrow third alert range which is completely contained in the wide third alert range and is narrower than the same. In the latter case, the user can select a desired one of the two first, second, or third alert ranges, through operation of keys (not shown) provided on the monitoring apparatus 8.

Meanwhile, each of the first, second, and third alert ranges $ATH_{EBP}$–$ATL_{EBP}$, $ATH_{RR}$–$ATL_{RR}$, $ATH_{VR}$–$ATL_{VR}$ may be replaced with only one of the upper and lower limit values $ATH_{EBP}$, $ATL_{EBP}$, $ATH_{RR}$, $ATL_{RR}$, $ATH_{VR}$, $ATL_{VR}$ of the each range. For example, the first to third alert ranges may be replaced with only the respective upper limit values $ATH_{EBP}$, $ATH_{RR}$, $ATH_{VR}$ thereof, or with only the respective lower limit values $ATL_{EBP}$, $ATL_{RR}$, $ATL_{VR}$ thereof. However, the single first upper limit value $ATH_{EBP}$ may be replaced with two first upper limit values, i.e., a great or high first upper limit value and a small or low first upper limit value, and the single first lower limit value $ATL_{EBP}$ may be replaced with two first lower limit values, i.e., a great or high first lower limit value and a small or low first lower limit value. Similarly, the single second upper limit value $ATH_{RR}$ may be replaced with two second upper limit values, i.e., a great or high second upper limit value and a small or low second upper limit value, the single second lower limit value $ATL_{RR}$ may be replaced with two second lower limit values, i.e., a great or high second lower limit value and a small or low second lower limit value, the single third upper limit value $ATH_{VR}$ may be replaced with two third upper limit values, i.e., a great or high third upper limit value and a small or low third upper limit value, and the single third lower limit value $ATL_{VR}$ may be replaced with two third lower limit values, i.e., a great or high third lower limit value and a small or low third lower limit value. In the latter case, the user can select a desired one of the two first, second, or third upper limit values, and a desired one of the two first, second, or third lower limit values, through operation of keys (not shown) provided on the monitoring apparatus 8.

For example, the graph displaying means 90 may display, in a two-dimensional coordinate system defined by a first axis indicative of time and a second axis indicative of BP-relating information, a graphical representation of a piece of BP-relating information obtained by the BP-relating-information obtaining means, and respective graphical representations of the alarm and alert ranges ALH–ALL, ATH–ATL. Otherwise, the graph displaying means 90 may display, in a three-dimensional coordinate system defined by three axes indicative of estimated BP value EBP, measured pulse-period value RR, and calculated pulse-wave-area value VR, respective graphical representations of an estimated BP value determined by the EBP determining means 78, a pulse period value RR measured by the pulse-period measuring means 82, and a pulse-wave area value VR calculated by the pulse-wave-area calculating means 84, and respective graphical representations of the three alarm ranges $ALH_{EBP}$–$ALL_{EBP}$, $ALH_{RR}$–$ALL_{RR}$, $ALH_{VR}$–$ALL_{VR}$ and the three alert ranges $ATH_{EBP}$–$ATL_{EBP}$, $ATH_{RR}$–$ATL_{RR}$, $ATH_{VR}$–$ATL_{VR}$.

Figure 6:
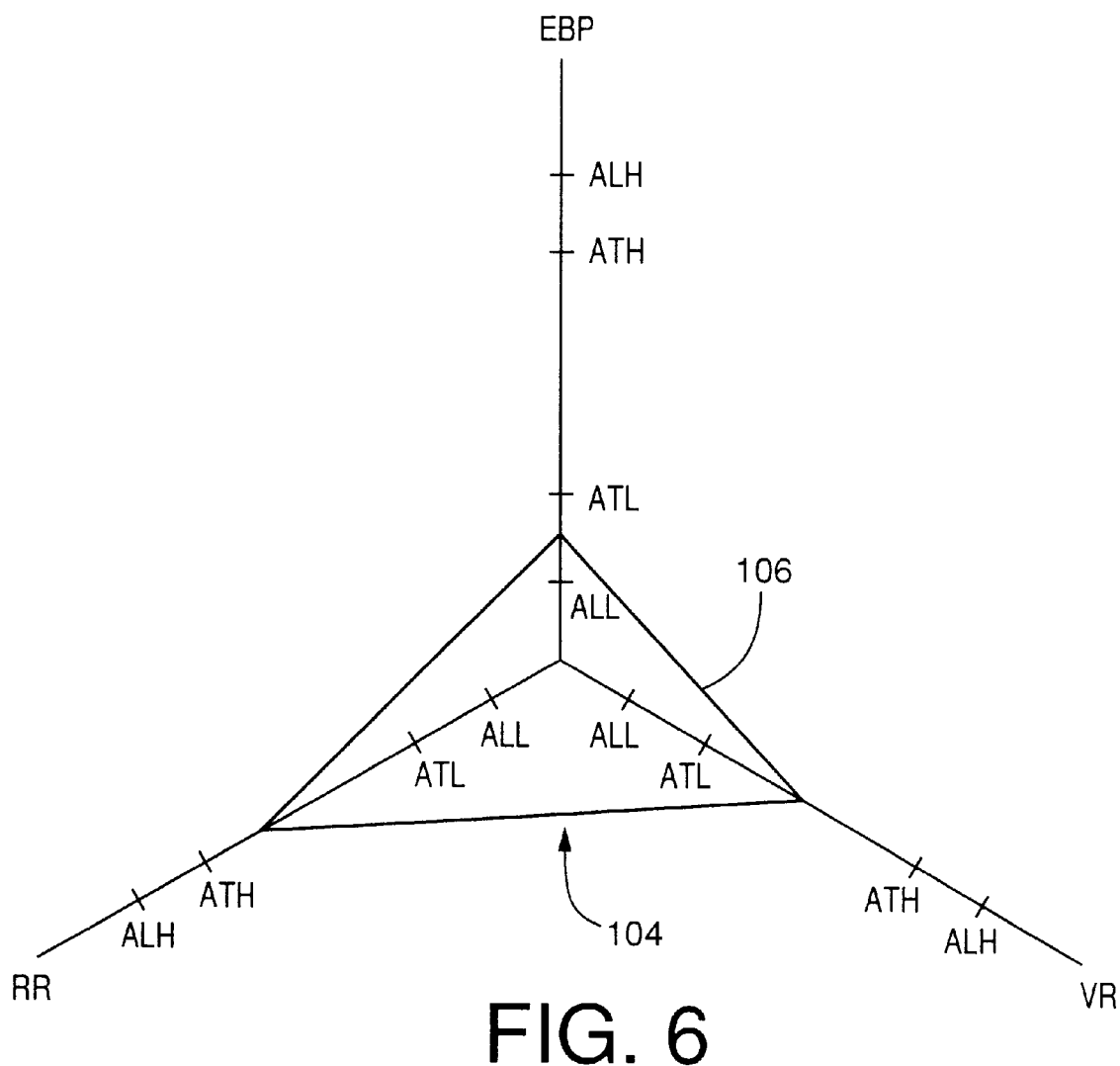
FIG. 6 is a view for illustrating a radar chart displayed by the display device of the apparatus of FIG. 1.

FIG. 5 and FIG. 6 show two examples of the graph displayed on the display device 32 by the graph displaying means 90, respectively. FIG. 5 shows a graph which is provided in a two-dimensional coordinate system defined by a first axis 92 indicative of time and a second axis 94 indicative of estimated BP value EBP and which includes an alarm range $ALH_{EBP}$–$ALL_{EBP}$ defined by an upper limit value $ALH_{EBP}$ represented by an upper solid line 96 and a lower limit value $ALL_{EBP}$ represented by a lower solid line 98, and an alert range $ATH_{EBP}$–$ATL_{EBP}$ defined by an upper limit value $ATH_{EBP}$ represented by an upper broken line 100 and a lower limit value $ALL_{EBP}$ represented by a lower broken line 102. The upper limit value $ATH_{EBP}$ of the alert range is smaller than that $ALH_{EBP}$ of the alarm range, and the lower limit value $ATL_{EBP}$ of the alert range is greater than that $ALL_{EBP}$ of the alarm range. Even if an estimated BP value EBP of the patient may fall outside the alert range 100–102, but if the value EBP falls within the alarm range 96–98, the BP-measurement starting means 86 does not start a BP measurement of the BP measuring means 70. However, it indicates that the patient or the medical person should be alert to the BP of the patient. The two-dimensional coordinate system additionally includes a trend graph of moving averages $EBP_{AV}$ of estimated BP values EBP iteratively determined by the EBP determining means 78. Each moving average $EBP_{AV}$ is an average of all estimated BP values EBP (e.g., about sixty values EBP) that have been determined in the last one minute and includes the last or current estimated BP value EBP. However, the trend graph of moving averages $EBP_{AV}$ may be replaced with a trend graph of estimated BP values EBP themselves. A symbol "O" (while circle) shown in FIG. 5 indicates a BP value measured by the BP measuring means 70 at the time of the last BP measuring operation. From the trend graph of the estimated BP values EBP (or the moving averages $EBP_{AV}$) each as a piece of BP-relating information utilized by the BP-measurement starting means 86, the patient or the medical person can predict a future change of the BP of the patient and judge whether the patient is near to a state in which the starting means 86 starts a BP measurement of the BP measuring means 70. Regarding the example shown in FIG. 5, the current estimated BP value EBP (or the current moving average $EBP_{AV}$) at the end of the trend graph falls between the lower broken line 102 and the lower solid line 98, indicating that the BP of the patient needs alerting.

FIG. 6 shows a radar chart 104, i.e., a three-dimensional coordinate system defined by three axes indicative of estimated BP value EBP, measured pulse-period value RR, and calculated pulse-wave-area value VR. The three axes meet one another at one point, i.e., origin. Each of the three axes is divided by respective graphical representations of an upper and a lower limit value ALH, ALL of an alarm range and an upper and a lower limit value ATH, ATL of an alert range. A triangle 106 functions as respective graphical representations of an estimated BP value determined by the EBP determining means 78, a pulse period value RR measured by the pulse-period measuring means 82, and a pulse-wave area value VR calculated by the pulse-wave-area calculating means 84. In this case, the plurality sorts of BP-relating information EBP, RR, VR all of which are utilized by the BP-measurement starting means 86 are concurrently displayed by the display device 32, and accordingly the patient or the medical person can judge whether the patient is near to the state in which the starting means 86 starts a BP measurement of the BP measuring means 70.

Figure 7:
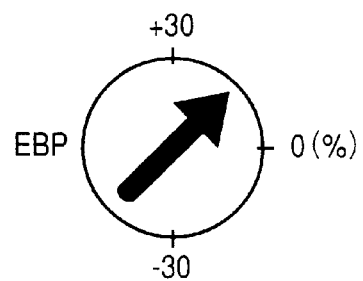
FIG. 7 is a view for illustrating a graphical representation of the ratio of the amount of change of an estimated BP value from the prior estimated BP value, to the prior estimated BP value, the graphical representation being displayed by the display device of the apparatus of FIG. 1.

A change displaying means or circuit 108 displays, on the display device 32, a graphical representation of a value relating to a change of each value EBP, RR, or VR iteratively determined as the piece of BP-relating information. The value relating to the change of each value EBP, RR or VR may be an amount of change of each value EBP, RR or VR from a moving average of a plurality of values EBP, RR or VR determined in the last predetermined time (e.g., in the last one minute), or from its prior value EBP, RR or VR, or the ratio of the amount of change to the moving average or the prior value. FIG. 7 shows an example of a graphical representation (i.e., a rotary arrow) of the ratio of the amount of change of each value EBP from its prior value EBP, to the prior value EBP, displayed by the change displaying means 108. From the graph shown in FIG. 7, the patient or the medical person can more easily judge whether the patient is near to the state in which the starting means 86 starts a BP measurement of the BP measuring means 70. The graph shown in FIG. 5 or FIG. 6 only shows a positional relationship between the current BP-relating information such as the current estimated BP value and the alarm and alert ranges ALH–ALL, ATH–ATL. The graph shown in FIG. 7 additionally shows a current tendency of change of the BP-relating information obtained from the patient.

Next, there will be described the operation of the control device 28 of the BP monitoring apparatus 8 by reference to the flow charts of FIGS. 8 and 9. The flow chart of FIG. 8 represents the BP monitoring routine, and the flow chart of FIG. 9 represents the BP-measurement-start judging routine.

Figure 8:
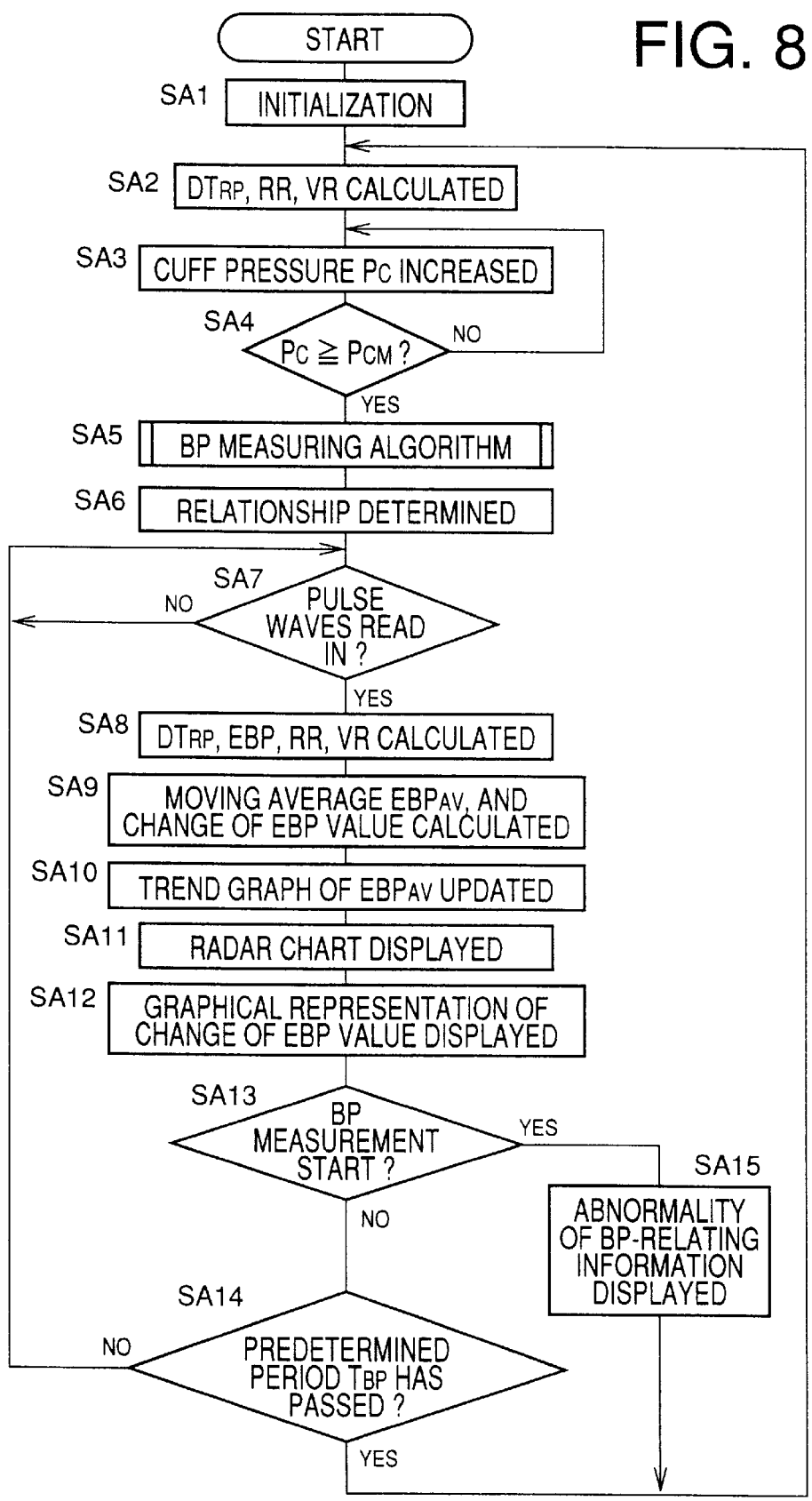
FIG. 8 is a flow chart representing a control program according to which the control device of the apparatus of FIG. 1 is operated for monitoring the BP of a living subject.
Figure 9:
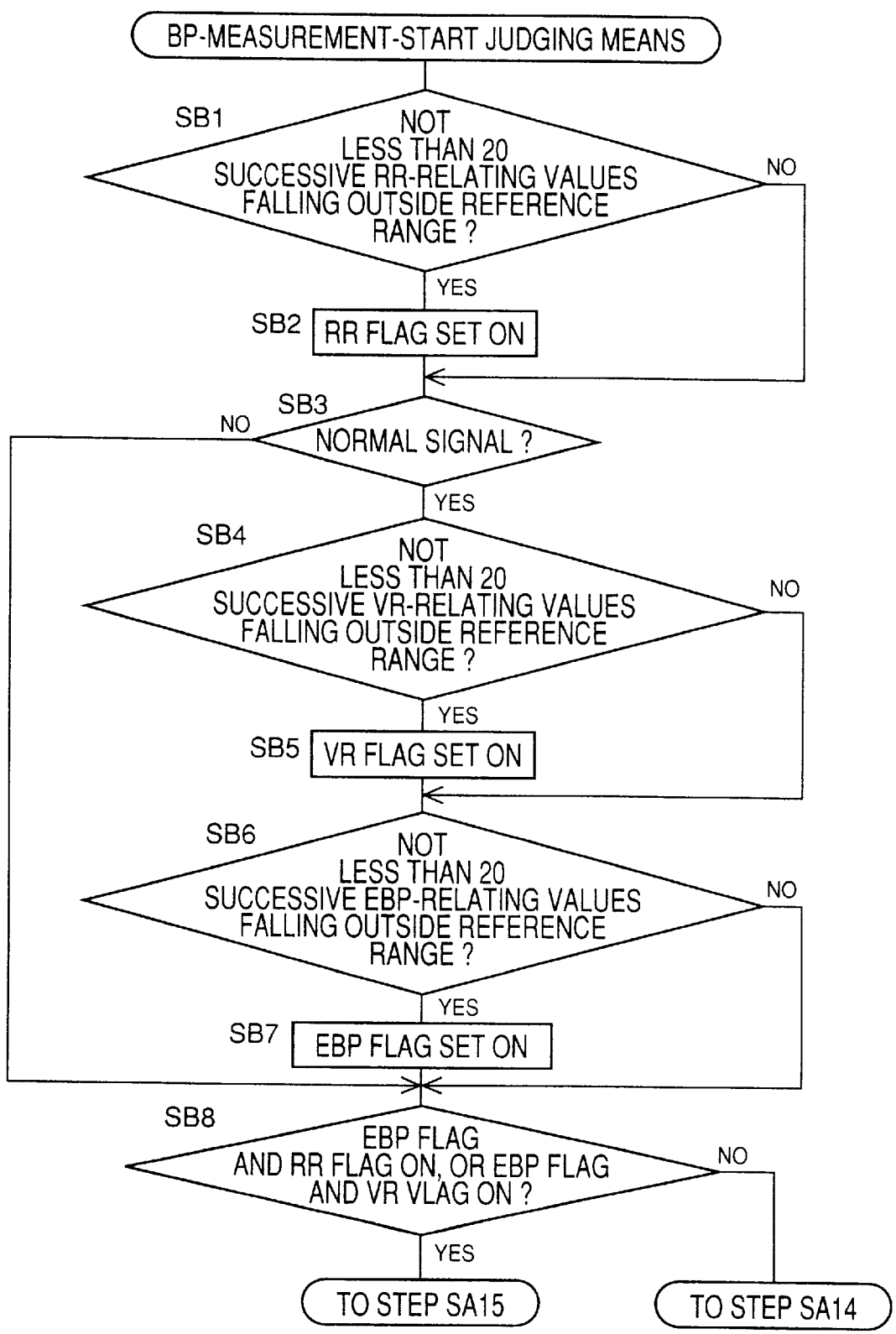
FIG. 9 is a BP-measurement-start judging routine carried out at Step SA13 of FIG. 8.

The control of the CPU 29 begins with Step SA1 of the flow chart of FIG. 8, where flags, counters, and registers (not shown) are reset, that is, the initialization of the control device 28 is carried out. Step SA1 is followed by Step SA2 to calculate, as a PWP time value $DT_{RP}$, a time difference between a R-wave of the waveform of a heartbeat-synchronous pulse of the ECG pulse wave and a rising point of the waveform of a corresponding pulse of the photoelectric pulse wave ("PPW") which are obtained immediately before the increasing of the cuff pressure. Step SA2 corresponds to the PWP-relating-information obtaining means 74. In addition, the CPU 29 calculates a pulse period value RR based on the time interval between two successive pulses of the ECG pulse wave, and calculates a normalized pulse-wave area value VR from the waveform of a pulse of the PPW. Thus, Step SA2 also corresponds to the pulse-period measuring means 82 and the pulse-wave-area calculating means 84.

The control of the CPU 29 goes to Steps SA3 and SA4 corresponding to the cuff-pressure control means 72. At Step SA3, the CPU 29 quickly increases the cuff pressure $P_C$ for a BP measurement of the BP measuring means 70, by switching the selector valve 16 to the inflation position and operating the air pump 18. Step SA3 is followed by Step SA4 to judge whether the cuff pressure $P_C$ is equal to or greater than a predetermined target pressure value $P_{CM}$ (e.g., 180 mmHg). If a negative judgement is made at Step SA4, the control of the CPU 29 goes back to Step SA2 so as to continue increasing the cuff pressure $P_C$.

If a positive judgement is made at Step SA4, the control of the CPU 29 goes to Step SA5 to carry out a BP measuring algorithm. More specifically described, the air pump 18 is stopped and the selector value 16 is switched to the slow-deflation position where the valve 16 permits the pressurized air to be slowly discharged from the cuff 10. A systolic BP value $BP_{SYS}$, a mean BP value $BP_{MEAN}$, and a diastolic BP value $BP_{DIA}$ are determined, according to a well known oscillometric BP determining algorithm, based on the variation of respective amplitudes of heartbeat-synchronous pulses of the pulse wave represented by the cuff-pulse-wave signal $SM_1$ obtained while the cuff pressure $P_C$ is slowly decreased at a predetermined rate of about 3 mmHg/sec, and a heart rate value HR is determined based on the interval between two successive pulses of the pulse wave. The thus measured BP values and heart rate HR are displayed on the display device 32, and the selector valve 16 is switched to the quick-deflation position where the valve 16 permits the pressurized air to be quickly discharged from the cuff 10. Step SA5 corresponds to the BP measuring means 70.

Step SA5 is followed by Step SA6 to determine a relationship between PWP time value $DT_{RP}$ and estimated BP value EBP based on two BP values measured at Step SA5 in two control cycles each according to the flow chart of FIG. 8, and two PWP time values $DT_{RP}$ calculated at Step SA2 in the two control cycles. More specifically described, when the systolic, mean, and diastolic BP values $BP_{SYS}$, $BP_{MEAN}$, $BP_{DIA}$ are measured at Step SA5, then at Step SA6 a relationship between PWP time value $DT_{RP}$ and estimated systolic, mean, or diastolic BP value $EBP_{SYS}$, $EBP_{MEAN}$, $EBP_{DIA}$, represented by the expression (2), is determined based on the two systolic, mean, or diastolic BP values $BP_{SYS}$, $BP_{MEAN}$, $BP_{DIA}$ measured at Step SA5 in the last two control cycles including the last or current control cycle, and the two PWP time values $DT_{RP}$ calculated at Step SA2 in the last two control cycles. Step SA6 corresponds to the relationship determining means 76. In addition, the CPU 29 determines an estimated BP value EBP of the patient based on the PWP time value $DT_{RP}$ determined at Step SA2, according to the thus determined relationship.

Step SA6 is followed by Step SA7 to judge whether an R-wave of the waveform of a heartbeat-synchronous pulse of the ECG pulse wave and a rising point of the waveform of a corresponding pulse of the PPW have been read in. If a negative judgment is made at Step SA7, the control of the CPU 29 waits until a positive judgment is made at Step SA7. On the other hand, if a positive judgment is made at Step SA7, the control of the CPU 29 goes to Step SA8 corresponding to the PWP-relating-information obtaining means 74, the EBP determining means 78, the pulse-period measuring means 82, and the pulse-wave-area calculating means 84. At Step SA8, the CPU 29 calculates a PWP time value $DT_{RP}$, a pulse period value RR, and a pulse-wave area value VR, based on the respective pulses of the ECG pulse wave and the PPW newly input at Step SA7, in the same manner as that employed at Step SA2. In addition, the CPU 29 determines an estimated BP value EBP based on the calculated PWP time value $DT_{RP}$ according to the relationship determined at Step SA6.

Step SA8 is followed by Step SA9 where the CPU 29 calculates a moving average $EBP_{AV}$ of the estimated BP values EBP which have been determined in the last one minute and which includes the current estimated BP value EBP determined at Step SA8 in the current control cycle, and additionally calculates the ratio of the amount of change of the current estimated BP value EBP determined at Step SA8 in the current control cycle from the prior value EBP determined at Step SA8 in the prior control cycle, to the prior value EBP.

Step SA9 is followed by Steps SA10 and SA11 corresponding to the graph displaying means 90. The CPU 29 controls the display device 32 to display respective graphical representations of the estimated BP value EBP, the pulse period value RR, and the pulse-wave area value VR determined at Step SA8. First, at Step SA10, the display device 32 displays, in the two-dimensional coordinate system defined by the time axis 92 and the EBP axis 94, the trend graph of the moving averages $EBP_{AV}$ including the current moving average $EBP_{AV}$ determined at Step SA9 in the current control cycle, as shown in FIG. 5.

Next, at Step SA11, the display device 32 displays the triangle 106 graphically representing the estimated BP value EBP, the pulse period value RR, and the pulse-wave area value VR determined at Step SA8, in the radar chart 104 defined by the three axes which are indicative of estimated BP value EBP, pulse period value RR, and pulse-wave area value VR, respectively, and each of which is divided by the upper and lower limit values ALH, ALL of a predetermined alarm range and the upper and lower limit values ATH, ATL of a predetermined alert range, as shown in FIG. 6.

Step SA11 is followed by Step SA12 corresponding to the change displaying means 108. At Step SA12, the CPU 29 controls the display device 32 to display an arrow representing the ratio, determined at Step SA9, relating to the change of the current estimated BP value determined at Step SA8, as shown in FIG. 7.

Step SA12 is followed by Step SA13 corresponding to the BP-measurement starting means 86. At Step SA13, the CPU 29 starts a BP measurement of the BP measuring means 70, when the estimated BP value EBP is judged as being abnormal and simultaneously at least one of the measured pulse period value RR and the calculated pulse-wave area value VR is judged as being abnormal, as a result of the execution of the BP-measurement-start judging routine of FIG. 9.

At Step SB1 of FIG. 9 corresponding to the RR-abnormality judging means 88, the CPU 29 judges whether the pulse period value RR calculated at Step SA8 of FIG. 8 is abnormal. For instance, the CPU 29 judges that the pulse period value RR is abnormal when the state in which the pulse period value RR measured at Step SA8 in each control cycle falls outside the predetermined alarm range $ALH_{RR}$–$ALL_{RR}$ has continued for a time period corresponding to not less than a predetermined number of pulses (e.g., 20 pulses). If a negative judgment is made at Step SB1, the control of the CPU 29 skips Step SB2 and goes to Step SB3. On the other hand, if a positive judgment is made at Step SB1, the control goes to Step SB2 where an RR flag is set "ON" so as to indicate the abnormality of the pulse period value RR.

Step SB2 is followed by Step SB3 to judge whether the PPW signal $SM_3$ detected from the peripheral portion (i.e., finger) of the patient is normal. At Step SB3, the CPU 29 removes an abnormal waveform from the PPW signal $SM_3$. For example, the CPU 29 removes, from the PPW signal $SM_3$, the waveform of each pulse, if the inclination of base line of the waveform of each pulse is greater than a reference angle, or if the waveform has a deformation due to a calibration of the monitoring apparatus 8. If a negative judgment is made at Step SB3, the control of the CPU 29 goes to Step SB8. On the other hand, if a positive judgement is made at Step SB3, the control of the CPU 29 goes to Step SB4.

At Step SB4 corresponding to the VR-abnormality judging means 89, the CPU 29 judges whether the normalized pulse-wave area value VR calculated at Step SA8 is abnormal. For instance, the CPU 29 judges that the pulse-wave area value VR is abnormal when the state in which the pulse-wave area value VR calculated at Step SA8 in each control cycle falls outside the predetermined alarm range $ALH_{VR}$–$ALL_{VR}$ has continued for a time period corresponding to not less than a predetermined number of pulses (e.g., 20 pulses). If a negative judgment is made at Step SB4, the control of CPU 29 goes to Step SB6. On the other hand, if a positive judgment is made at Step SB4, the control of the CPU 29 goes to Step SB5 where a VR flag is set "ON" so as to indicate the abnormality of the pulse-wave area value VR.

Step SB5 is followed by Step SB6 corresponding to the EBP-abnormality judging means 87. At Step SB6, the CPU 29 judges whether the estimated BP value EBP determined at Step SA8 is abnormal. For instance, the CPU 29 judges that the estimated BP value EBP determined at Step SA8 is abnormal when the state in which the estimated BP value EBP determined in each control cycle falls outside the predetermined alarm range $ALH_{EBP}$–$ALL_{EBP}$ has continued for a time period corresponding to not less than a predetermined number of pulses (e.g., 20 pulses). If a negative judgment is made at Step SB6, the control of the CPU 29 goes to Step SB8. On the other hand, if a positive judgment is made at Step SB6, the control of the CPU 29 goes to Step SB7 where an EBP flag is set "ON" so as to indicate the abnormality of the estimated BP value EBP.

Step SB7 is followed by Step SB8 to judge whether the EBP flag is "ON" and simultaneously at least one of the RR flag and the VR flag is "ON". If a negative judgment is made at Step SB8, the control of the CPU 29 goes to Step SA14. At Step SA14, the CPU 29 judges whether a predetermined period (e.g., 20 minutes), that is, a calibration period, has passed after the last BP measuring operation has been carried out using the inflatable cuff 10 at Step SA5 of FIG. 8. If a negative judgment is made at Step SA14, the control of the CPU 29 goes back to Step SA7 and the following steps so as to carry out a BP monitoring control cycle. On the other hand, if a positive judgment is made at Step SA14, the control of the CPU 29 goes back to Step SA2 and the following steps so as to carry out a calibration control cycle, i.e., determine a new relationship between PWP time value $DT_{RP}$ and estimated BP value EBP.

Meanwhile, if a positive judgment is made at Step SB8, the control of the CPU 29 goes to Step SA15 of FIG. 8. At Step SA15, the CPU 29 controls the display device 32 to display one or more symbols or messages indicative of the abnormality of one or more of the estimated BP value EBP, the measured pulse period value RR, and the pulse-wave area value VR for which one or more of the RR, VR, and EBP flags has or have been set "ON" at Steps SB2, SB5, and SB7. Then, the control of the CPU 29 goes back to Step SA2 of the BP measuring routine of FIG. 8 so as to start a BP measurement using the cuff 10 and determine a new relationship between PWP time value $DT_{RP}$ and estimated BP value EBP.

In the present embodiment, the graph displaying means 90 displays, in the two-dimensional coordinate system which is provided in the screen image displayed on the display device 32 and which is defined by the time axis 92 and the EBP axis 94, a graphic representation of each estimated BP value EBP (or each moving average $EBP_{AV}$) iteratively determined by the EBP determining means 78 and a graphic representation of the predetermined alarm range $ALH_{EBP}$–$ALL_{EBP}$, so that the two graphic representations can be compared with each other by the patient or the medical person. From the positional relationship between each estimated BP value EBP (or $EBP_{AV}$) and the alarm range $ALH_{EBP}$–$ALL_{EBP}$ in the coordinate system, the patient or the medical person can judge whether the BP of the patient is near to the state in which a BP measurement of the BP measuring means 70 is started.

In addition, in the present embodiment, the graph displaying means 90 displays respective graphical representations of the estimated BP value EBP determined by the EBP determining means 78, the pulse period value RR measured by the pulse-period measuring means 82, and the pulse-wave area value VR calculated by the pulse-wave-area calculating means 84, in the radar chart 104 defined by the three axes each of which is divided by the upper and lower limit values of a corresponding one of the three predetermined alarm ranges $ALH_{EBP}$–$ALL_{EBP}$, $ALH_{RR}$–$ALL_{RR}$, $ALH_{VR}$–$ALL_{VR}$, so that the graphical representations of the values EBP, RR, VR can be compared with respective graphical representations of the upper and lower values $ALH_{EBP}$, $ALL_{EBP}$, $ALH_{RR}$, $ALL_{RR}$, $ALH_{VR}$, $ALL_{VR}$ of the three alarm ranges by the patient or the medical person. From the positional relationship between the three determined values EBP, RR, VR and the three alarm ranges $ALH_{EBP}$–$ALL_{EBP}$, $ALH_{RR}$–$ALL_{RR}$, $ALH_{VR}$–$ALL_{VR}$ in the radar chart 104, the patient or the medical person can judge whether the BP of the patient is near to the state in which a BP measurement of the BP measuring means 70 is started.

Moreover, in the present embodiment, the graph displaying means 90 displays the graphical representation of each estimated BP value EBP (or each moving average $EBP_{AV}$), with the graphical representation of the alarm range $ALH_{EBP}$–$ALL_{EBP}$ and the graphical representation of the alert range $ALH_{EBP}$–$ALL_{EBP}$ completely contained in the alarm range and narrower than the same, so that the graphical representation of each value EBP (or $EBP_{AV}$) can be compared with the respective graphical representations of the two ranges by the patient or the medical person. Thus, the patient or the medical person can more easily judge whether the BP of the patient is near to the state in which a BP measurement of the BP measuring means 70 is started.

Furthermore, in the present embodiment, the graph displaying means 90 displays the respective graphical representations of each estimated BP value EBP, each measured pulse period value RR, and each calculated pulse-wave area value VR, in the radar chart 104 defined by the three axes each of which is divided by the upper and lower limit values of a corresponding one of the three predetermined alarm ranges $ALH_{EBP}$–$ALL_{EBP}$, $ALH_{RR}$–$ALL_{RR}$, $ALH_{VR}$–$ALL_{VR}$, and the upper and lower limit values of a corresponding one of the three predetermined alert ranges $ATH_{EBP}$–$ATL_{EBP}$, $ATH_{RR}$–$ATL_{RR}$, $ATH_{VR}$–$ATL_{VR}$, so that the graphical representations of the values EBP, RR, VR can be compared with the respective graphical representations of the upper and lower values $ALH_{EBP}$, $ALL_{EBP}$, $ALH_{RR}$, $ALL_{RR}$, $ALH_{VR}$, $ALL_{VR}$ of the three alarm ranges and respective graphical representations of the upper and lower values $ATH_{EBP}$, $ATL_{EBP}$, $ATH_{RR}$, $ATL_{RR}$, $ATH_{VR}$, $ATL_{VR}$ of the three alert ranges by the patient or the medical person. Thus, the patient or the medical person can more easily judge whether the BP of the patient is near to the state in which a BP measurement of the BP measuring means 70 is started.

The present BP monitoring apparatus 8 includes the change displaying means 108 which displays, on the display device 32, a value relating to a change of each estimated BP value EBP from a value based on at least one prior estimated BP value EBP. The value relating to the change may be the ratio of the amount of change of each value EBP from its prior value EBP, to the prior value EBP. Thus, the display device 32 displays, in addition to the graph representing the positional relationship between each estimated BP value EBP (or each moving average $EBP_{AV}$) and the alarm range $ATH_{EBP}$–$ATL_{EBP}$, the graph representing the tendency of change of each value EBP and thus indicating a future change of the BP of the patient. Accordingly, the patient or the medical person can more accurately judge whether the BP of the patient is changing toward the state in which a BP measurement of the BP measuring means 70 is started.

While the present invention has been described in its preferred embodiment by reference to the drawings, it is to be understood that the invention may otherwise be embodied.

While in the illustrated embodiment the BP-measurement starting 86 starts a BP measurement of the BP measuring means 70, when it is judged at Step SB8 that the EBP flag is "ON" and at least one of the RR flag and the VR flag is "ON". However, the BP-measurement starting means 86 may be adapted to start a BP measurement of the BP measuring means 70, when it is judged at Step SB8 that at least one of the EBP flag, the RR flag, and the VR flag is "ON", because each of the parameters EBP, RR, VR changes in relation with the change of BP of a living subject.

At Step SB7, the EBP flag may be set "ON" only if it is judged at Step SB6 that a single estimated BP value EBP determined in each control cycle falls outside the predetermined alarm range $ALH_{EBP}$–$ALL_{EBP}$. This is also true with Steps SB1 and SB2, and with Steps SB4 and SB5.

At Steps SB6 and SB7, the parameter $DT_{RP}$ or $V_M$ may be employed in place of the parameter EBP, because each value $DT_{RP}$, $V_M$ corresponds to each value EBP, one by one, as defined by the second or third expression (2), (3).

In the illustrated embodiment, the pulse period RR (sec) may be replaced with heart rate HR (1/min), because the heart rate HR corresponds to the pulse period RR, one to one, according to the following expression: HR=60/RR. Therefore, the pulse-period measuring means 82 and the RR-abnormality judging means 88 may be replaced with heart-rate measuring means and HR-abnormality judging means, respectively.

Figure 10:
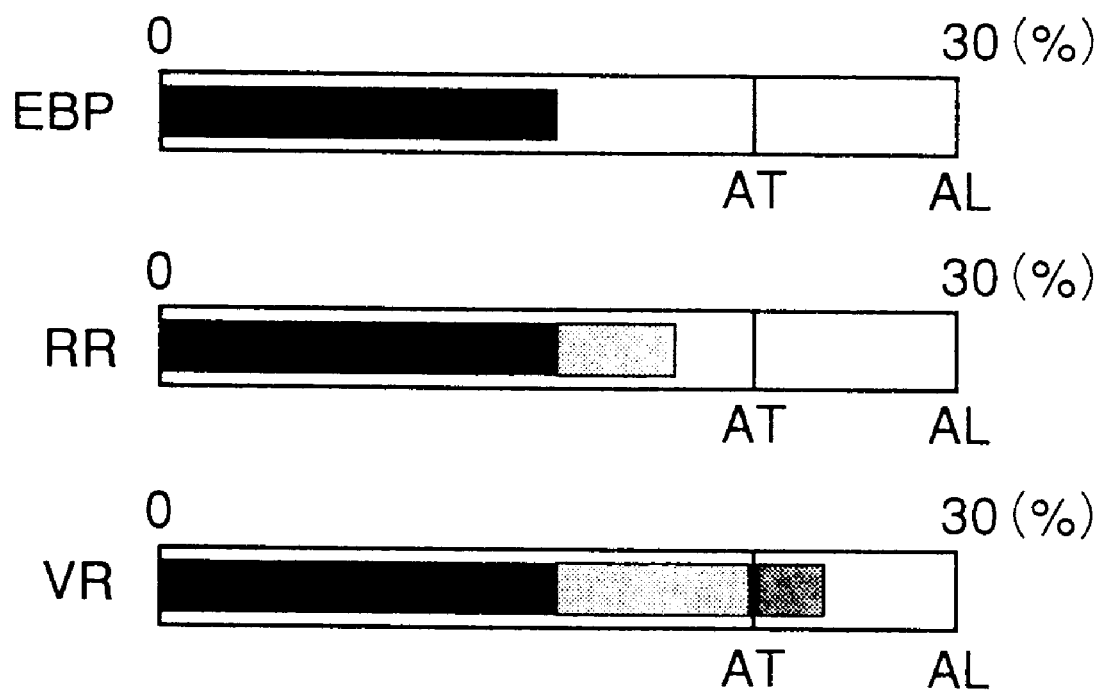
FIG. 10 is a view for illustrating a graphical representation of the ratio of the amount of change of an estimated BP value from a certain prior estimated BP value, to the prior estimated BP value, a graphical representation of the ratio of the amount of change of a pulse period value from a certain prior pulse period value, to the prior pulse period value, and a graphical representation of the ratio of the amount of change of a pulse-wave area value from a certain prior pulse-wave area value, to the prior pulse-wave area value, the three graphical representations being concurrently displayed by the display device of the apparatus of FIG. 1.

In the illustrated embodiment, the graph displaying means 90 displays, at Step SA11, the respective graphical representations of each estimated BP value EBP, each measured pulse period value RR, and each calculated pulse-wave area value VR, in the radar chart 104 defined by the three axes each of which is divided by the upper and lower limit values of a corresponding one of the three predetermined alarm ranges and the upper and lower limit values of a corresponding one of the three predetermined alert ranges. However, the radar chart 104 may be replaced with three bar graphs, as shown in FIG. 10, representing the respective absolute values of respective ratios determined for each estimated BP value EBP, each measured pulse period value RR, and each calculated pulse-wave area value VR, respectively. A ratio determined for each value EBP, RR, or VR is the ratio of the amount of change of each value EBP, RR, or VR from a "control" value EBP, RR, or VR determined at the time of the last BP measuring operation, to the "control" value EBP, RR, or VR. The display device 32 displays, with each of the three bar graphs EBP, RR, VR, a corresponding one of three alarm values $AL_{EBP}$, $AL_{RR}$, $AL_{VR}$ and a corresponding one of three alert values $AT_{EBP}$, $AT_{RR}$, $AT_{VR}$.

Figure 11:
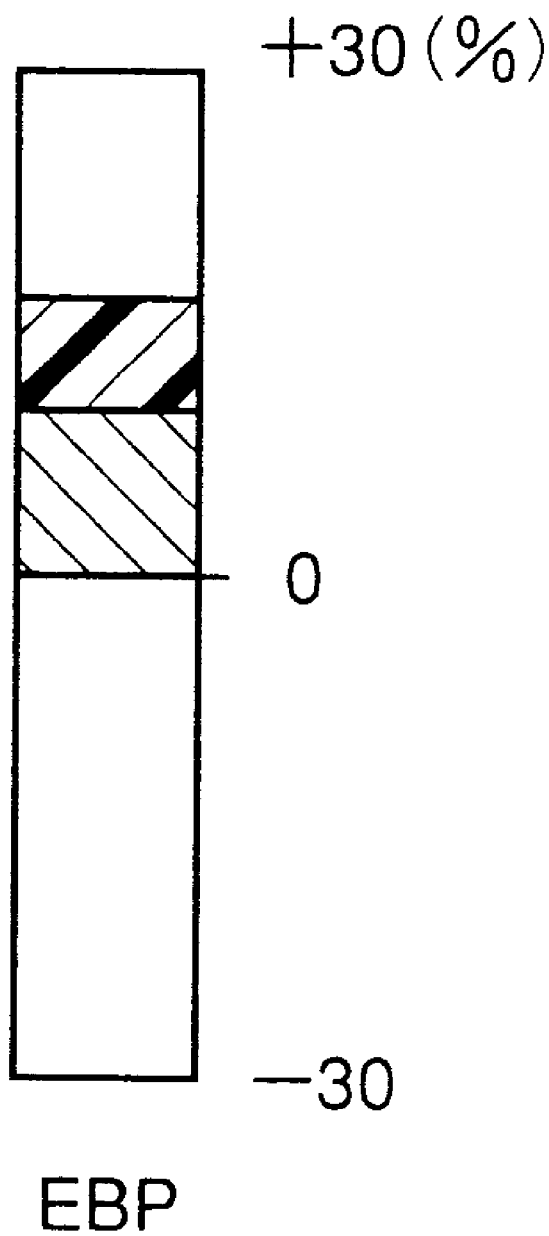
FIG. 11 is a view for illustrating another graphical representation of the ratio of the amount of change of an estimated BP value from the prior estimated BP value, to the prior estimated BP value, the graphical representation being displayed by the display device of the apparatus of FIG. 1.

In the illustrated embodiment, the change displaying means 108 displays the rotary arrow, shown in FIG. 7, representing the value relating to the change of each estimated BP value EBP. However, the rotary arrow of FIG. 7 may be replaced with a bar graph as shown in FIG. 11.

It is to be understood that the present invention may be embodied with other changes, improvements, and modifications that may occur to one having skill in the art without departing from the spirit and scope of the invention defined in the appended claims.

What is claimed is:

1. A blood-pressure monitoring apparatus comprising:

a measuring device which includes an inflatable cuff adapted to apply a pressing pressure to a first body portion of a living subject and which measures a blood-pressure value of the living subject by changing the pressing pressure of the inflatable cuff;

a blood-pressure-relating-information obtaining device which iteratively obtains a piece of blood-pressure-relating information which changes in relation to a change of the blood pressure of the living subject;

starting means for starting, when the obtained blood-pressure-relating information satisfies a predetermined condition with respect to at least one reference value, a blood-pressure measurement of the measuring device; and a display device which displays a first graphical representation of the obtained blood-pressure-relating information, and a second graphical representation of the reference value, so that the first graphical representation is comparable with the second graphical representation.

2. An apparatus according to claim 1, wherein the blood-pressure-relating-information obtaining device comprises at least one of pulse-wave-propagation-time calculating means for iteratively calculating, as the obtained blood-pressure-relating information, a pulse-wave propagation time which is needed for each of a plurality of heartbeat-synchronous pulses of a pulse wave to propagate between two portions of an arterial vessel of the living subject, and pulse-wave-propagation-velocity calculating means for iteratively calculating, as the obtained blood-pressure-relating information, a pulse-wave propagation velocity at which each of a plurality of heartbeat-synchronous pulses of a pulse wave propagates between two portions of an arterial vessel of the living subject.

3. An apparatus according to claim 1, wherein the blood-pressure-relating-information obtaining device comprises at least one of pulse-period calculating means for iteratively calculating, as the obtained blood-pressure-relating information, a pulse period equal to a time interval between each pair of successive heartbeat-synchronous pulses of a pulse wave obtained from the living subject, and pulse-wave-area-relating-value calculating means for iteratively calculating, as the obtained blood-pressure-relating information, a pulse-wave-area-relating value relating to an area of each of a plurality of heartbeat-synchronous pulses of a pulse wave obtained from the living subject.

4. An apparatus according to claim 1, wherein the blood-pressure-relating-information obtaining device comprises at least one of an electrocardiographic-pulse-wave detecting device which includes a plurality of electrodes adapted to be put on a plurality of portions of the living body and detects an electrocardiographic pulse wave including a plurality of heartbeat-synchronous pulses, from the subject via the electrodes, and a photoelectric-pulse-wave detecting device which is adapted to be worn on a second body portion of the living subject, and which emits a light toward the second body portion and obtains a photoelectric pulse wave including a plurality of heartbeat-synchronous pulses, from the light received from the second body portion.

5. An apparatus according to claim 1, wherein the display device comprises means for displaying the first graphical representation of the obtained blood-pressure-relating information, and the second graphical representation of the reference value, in a two-dimensional coordinate system which is defined by a first axis indicative of time and a second axis indicative of blood-pressure-relating information.

6. An apparatus according to claim 1, wherein the blood-pressure-relating-information obtaining device comprises means for iteratively obtaining three sorts of blood-pressure-relating information each of which changes in relation to a change of the blood pressure of the living subject, and wherein the display device comprises means for displaying the first graphical representation of each of the obtained three sorts of blood-pressure-relating information, and the second graphical representation of each of three reference values respectively corresponding to the three sorts of blood-pressure-relating information, in a three-dimensional coordinate system which is defined by a first axis indicative of a first one of the three sorts of blood-pressure-relating information, and a second axis indicative of a second one of the three sorts of blood-pressure-relating information, and a third axis indicative of a third one of the three sorts of blood-pressure-relating information.

7. An apparatus according to claim 1, wherein the blood-pressure-relating-information obtaining device comprises means for iteratively calculating a blood-pressure-relating value which changes in relation to a change of the blood pressure of the living subject, and wherein the starting means comprises means for starting the blood-pressure measurement of the measuring device, when a value based on the calculated blood-pressure-relating value satisfies the predetermined condition with respect to two reference values that the value based on the calculated blood-pressure-relating value does not fall within an alarm range having an upper limit value defined by one of the two reference values and a lower limit value defined by the other of the two reference values.

8. An apparatus according to claim 7, wherein the display device comprises means for displaying, with the first and second graphical representations, a third graphical representation of an alert range which is contained in the alarm range and is narrower than the alarm range, so that the first graphical representation is comparable with the second and third graphical representations.

9. An apparatus according to claim 1, wherein the blood-pressure-relating-information obtaining device comprises means for iteratively calculating a blood-pressure-relating value which changes in relation to a change of the blood pressure of the living subject, and wherein the starting means comprises means for starting the blood-pressure measurement of the measuring device, when a value based on the calculated blood-pressure-relating value satisfies the predetermined condition with respect to the reference value that the value based on the calculated blood-pressure-relating value is greater than the reference value.

10. An apparatus according to claim 9, wherein the display device comprises means for displaying, with the first and second graphical representations, a third graphical representation of an alert value which is smaller than the reference value, so that the first graphical representation is comparable with the second and third graphical representations.

11. An apparatus according to claim 1, wherein the blood-pressure-relating-information obtaining device comprises means for iteratively calculating a blood-pressure-relating value which changes in relation to a change of the blood pressure of the living subject, and wherein the starting means comprises means for starting the blood-pressure measurement of the measuring device, when a value based on the calculated blood-pressure-relating value satisfies the predetermined condition with respect to the reference value that the value based on the calculated blood-pressure-relating value is smaller than the reference value.

12. An apparatus according to claim 11, wherein the display device comprises means for displaying, with the first and second graphical representations, a third graphical representation of an alert value which is greater than the reference value, so that the first graphical representation is comparable with the second and third graphical representations.

13. An apparatus according to claim 1, wherein the blood-pressure-relating-information obtaining device comprises means for successively calculating, in synchronism with each of successive heartbeats of the living subject, a blood-pressure-relating value which changes in relation to a change of the blood pressure of the living subject, and wherein the display device comprises change displaying means for displaying, with the first and second graphical representations, a third graphical representation of a value relating to a change of each of the successively calculated blood-pressure-relating values, from a value based on at least one prior value of the successively calculated blood-pressure-relating values.

14. An apparatus according to claim 13, wherein the change displaying means comprises means for displaying the third graphical representation comprising an arrow which is rotatable from a predetermined original angle by an angle indicative of the value relating to the change of said each of the successively calculated blood-pressure-relating values.

15. An apparatus according to claim 13, wherein the change displaying means comprises means for displaying the third graphical representation of a ratio of an amount of change of said each blood-pressure-relating value from a prior blood-pressure-relating value which immediately precedes said each blood-pressure-relating value, to said prior blood-pressure-relating value.

16. An apparatus according to claim 1, wherein the blood-pressure-relating-information obtaining device comprises:

a pulse-wave-propagation-relating-information obtaining device which iteratively obtains a piece of pulse-wave-propagation-relating information relating to propagation of a pulse wave through an arterial vessel of the living subject;

relationship determining means for determining a relationship between pulse-wave-propagation-relating information and blood pressure, based on at least one blood-pressure value of the living subject measured by the measuring device and at least one piece of pulse-wave-propagation-relating information obtained by the pulse-wave-propagation-relating-information obtaining device; and estimating means for estimating a blood-pressure value of the living subject, based on each piece of pulse-wave-propagation-relating information of a plurality of pieces of pulse-wave-propagation-relating information obtained by the pulse-wave-propagation-relating-information obtaining device, according to the determined relationship between pulse-wave-propagation-relating information and blood pressure.

17. An apparatus according to claim 16, wherein the blood-pressure-relating-information obtaining device further comprises average calculating means for calculating, as the obtained blood-pressure-relating information, an average of a plurality of blood-pressure values estimated by the estimating means.

18. An apparatus according to claim 16, wherein the blood-pressure-relating-information obtaining device further comprises change-value calculating means for calculating, as the obtained blood-pressure-relating information, a value relating to a change of a first blood-pressure value estimated by the estimating means from a second blood-pressure value estimated prior to the first estimated blood-pressure value by the estimating means.

* * * * *